(12) United States Patent
Belyaev

(10) Patent No.: US 9,644,199 B2
(45) Date of Patent: May 9, 2017

(54) IMMOBILIZED TRANSPOSASE COMPLEXES FOR DNA FRAGMENTATION AND TAGGING

(71) Applicant: Agilent Technologies, Inc., Santa Clara, CA (US)

(72) Inventor: Alexander S Belyaev, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 508 days.

(21) Appl. No.: 13/960,837

(22) Filed: Aug. 7, 2013

(65) Prior Publication Data

US 2014/0093916 A1    Apr. 3, 2014

Related U.S. Application Data

(60) Provisional application No. 61/708,332, filed on Oct. 1, 2012.

(51) Int. Cl.
| | | |
|---|---|---|
| C12Q 1/68 | (2006.01) | |
| C12N 11/06 | (2006.01) | |
| C12N 9/12 | (2006.01) | |
| C12N 9/22 | (2006.01) | |

(52) U.S. Cl.
CPC ............ *C12N 11/06* (2013.01); *C12N 9/1241* (2013.01); *C12N 9/22* (2013.01)

(58) Field of Classification Search
CPC ......... C12N 11/06; C12N 9/1241; C12N 9/22
USPC ....................................................... 435/91.2
See application file for complete search history.

(56) References Cited

U.S. PATENT DOCUMENTS

| | | | |
|---|---|---|---|
| 2007/0172839 A1 | 7/2007 | Smith et al. | |
| 2009/0156415 A1 | 6/2009 | Remacle et al. | |
| 2010/0120098 A1* | 5/2010 | Grunenwald | C12N 15/10 435/91.2 |
| 2012/0208724 A1* | 8/2012 | Steemers | C12Q 1/6869 506/26 |

FOREIGN PATENT DOCUMENTS

| | | |
|---|---|---|
| EP | 2527438 A1 | 11/2012 |
| WO | 9837236 A1 | 8/1998 |
| WO | 2010048605 A1 | 4/2010 |
| WO | WO 2012106546 * | 8/2012 |

OTHER PUBLICATIONS

Nicholas Caruccio, "Preparation of Next-Generation Sequencing Libraries Using NexteraTM Technology: Simultaneous DNA Fragmentation and Adaptor Tagging by In Vitro Transposition," High-Throughput Next Generatio Sequencing Chapter 17 (Humana Press), pp. 240-255.
Syed et al., "Optimized library preparation method for next-generation sequencing," Nature Methods 6, (Oct. 2009) (2 pages), ISSN: 1548-7091, EISSN: 1548-7105, pp. i-ii.
Naumann T.A. etal., "Tn5 Transposase Active Site Mutants", *J. of Biological Chem*, 2002, vol. 277, No. 20, May 17, pp. 17623-17629.
Steiniger, Mindy et al., "Defining characteristics of Tn5 Transposase non-specific DNA binding", *Nucleic Acids Research*, 2006, vol. 34, No. 9, pp. 2820-2832.
Twining, Sally S. et al., "Functional Characterization of Arginine 30, Lysine 40, and Arginine 62 in Tn5 Transposase", *J. of Biological Chem.*, vol. 276, No. 25, Issue of Jun. 22, pp. 23135-23143.
Weinreich, Michael D. etal., Overexpression of the Tn5 Transposase in *Escherichia coli* Results in Filamentation, Aberrant Nucleiod Segregation, and Cell Death: Analysis of *E. coli* and Transposase Suppressor Mutations, *J. of Bacteriology*, Sep. 1994, p. 5494-5504, vol. 176, No. 17.

* cited by examiner

*Primary Examiner* — Cynthia B Wilder

(57) ABSTRACT

The present invention provides a simple and rapid method for preparing purified transposase complexes that are highly suited for fragmenting DNA. The method includes forming transposase complexes with oligonucleotide adapters in cell lysate, then purifying the complexes from the other substance in the cell lysate. Purification is accomplished using a specific binding pair, in which one member of the pair is bound to an oligonucleotide adapter of the complex and the other member of the pair is bound to a solid substrate. The bound complexes can be immediately used in DNA fragmentation reactions to produce solid substrate-bound DNA fragments, which can be used for any number of purposes, including as templates for amplification and sequencing.

3 Claims, 17 Drawing Sheets

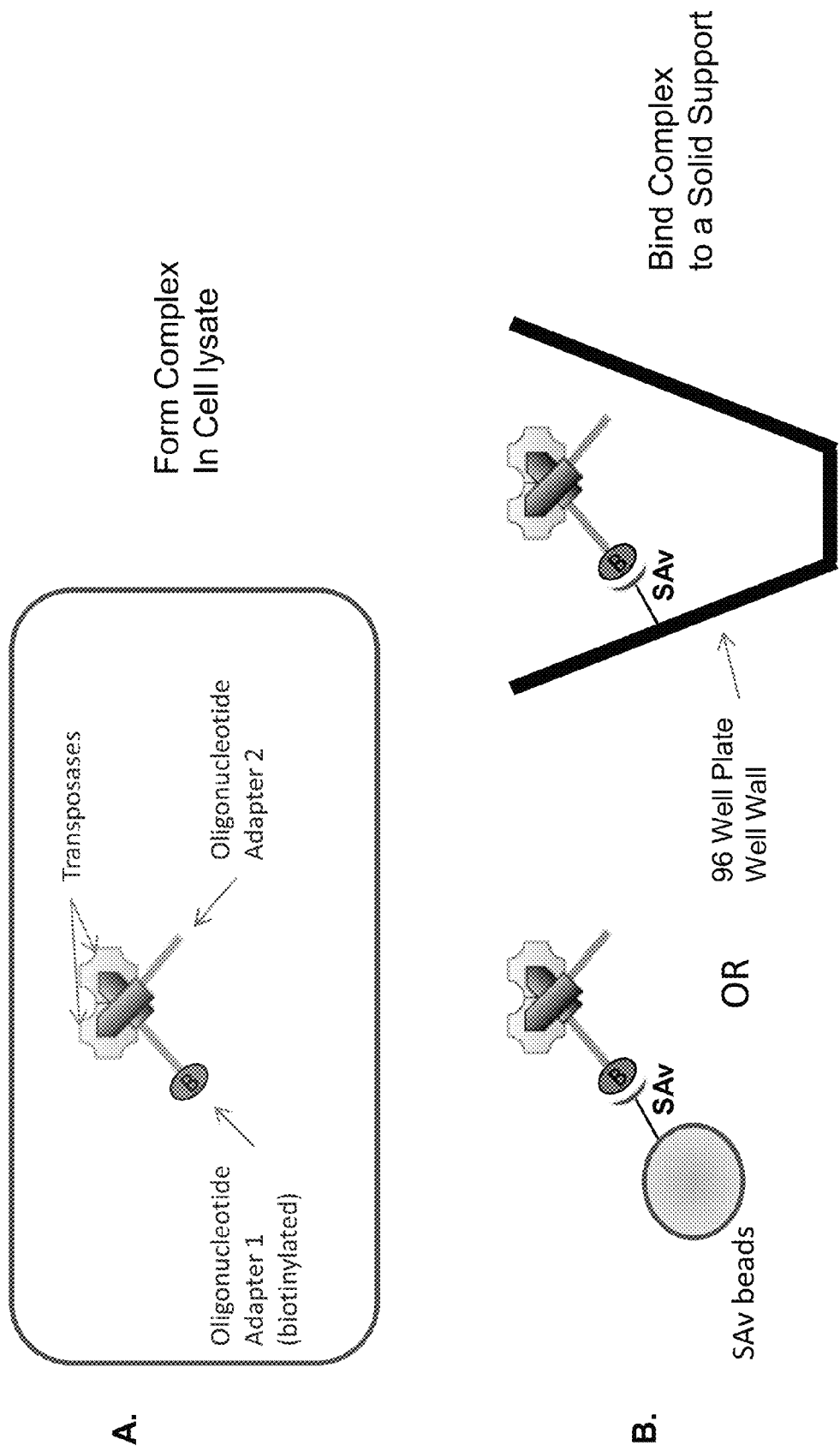

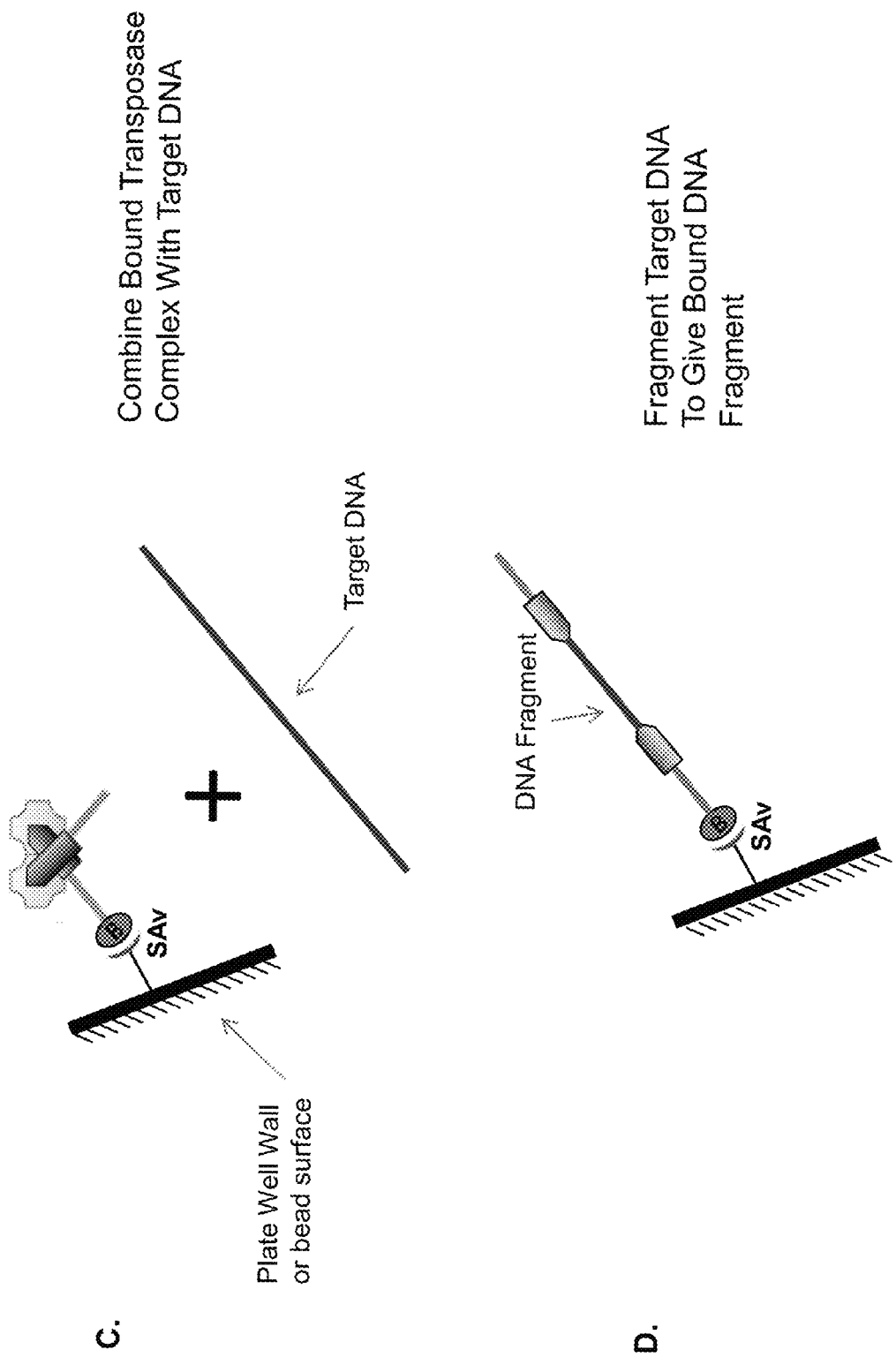
Figure 1, cont.

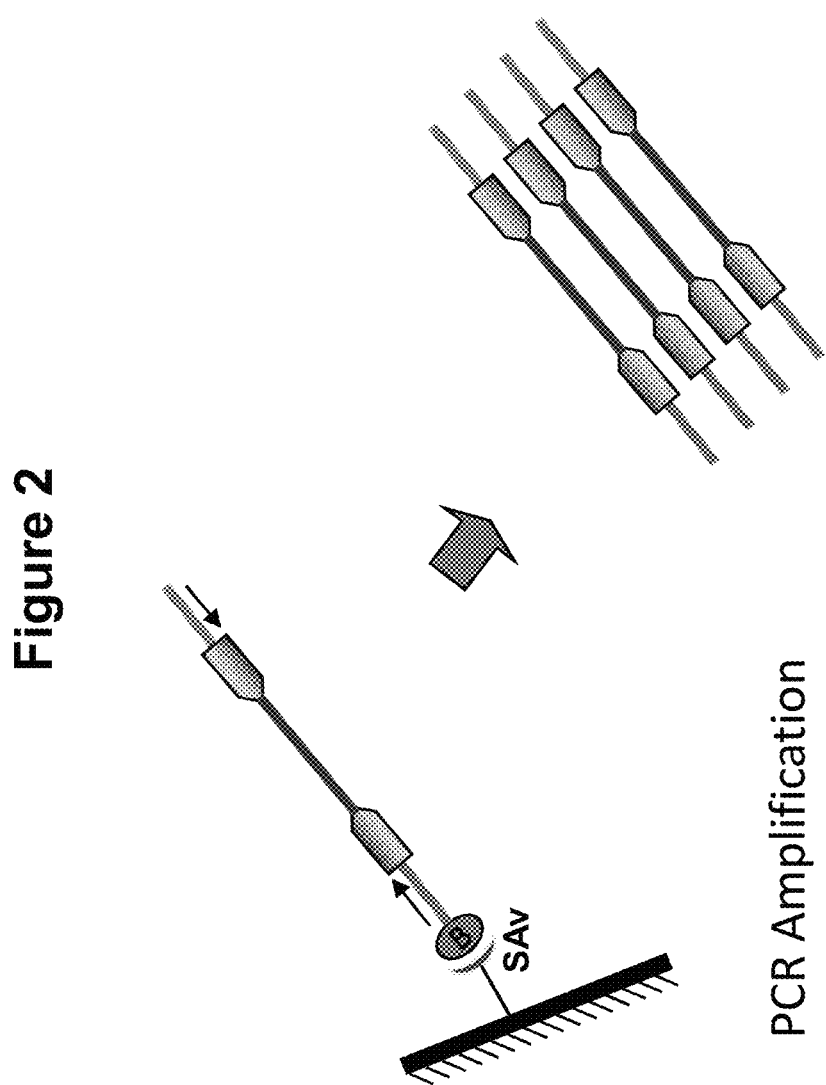

Figure 9, cont.
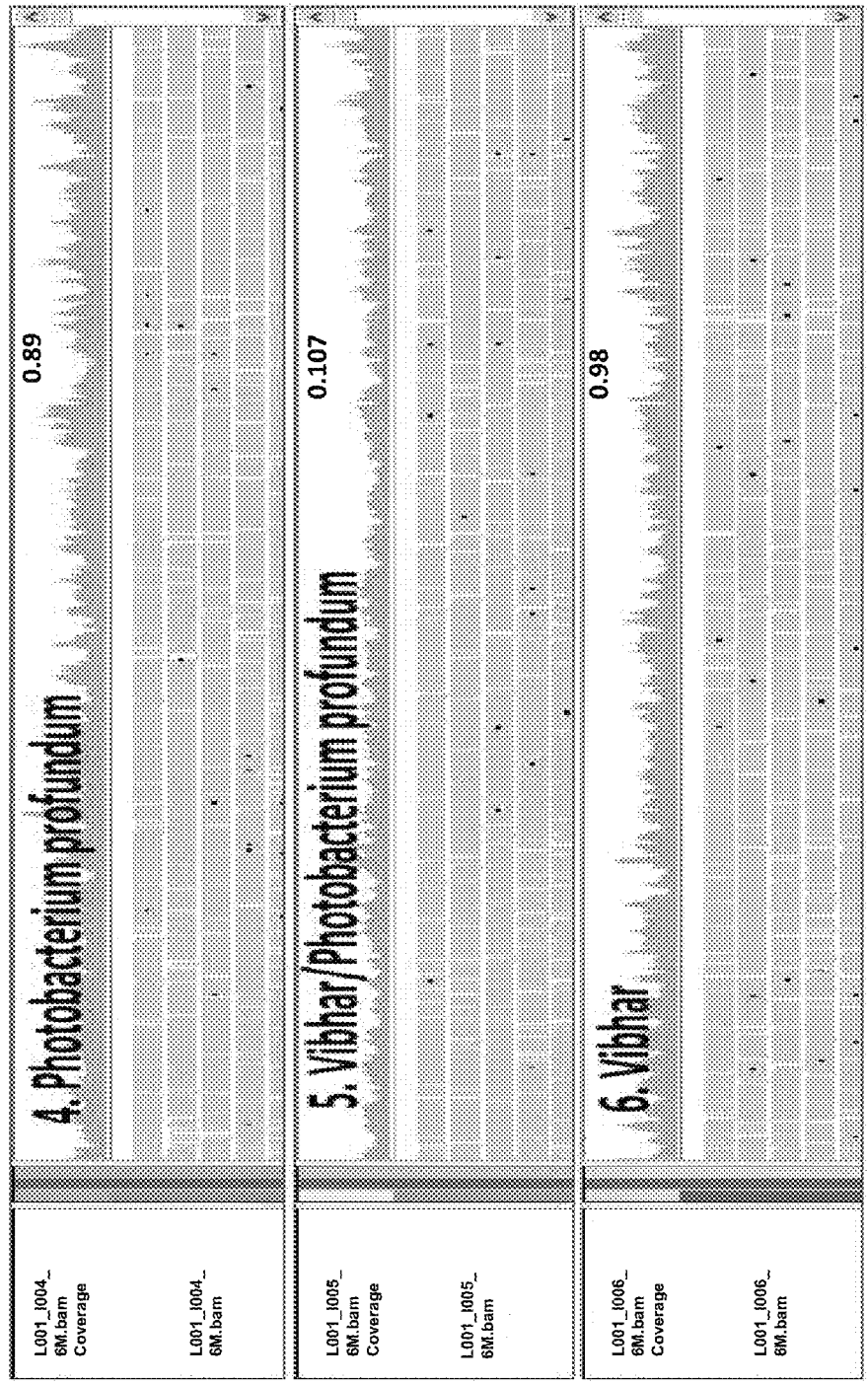

Figure 10, cont.
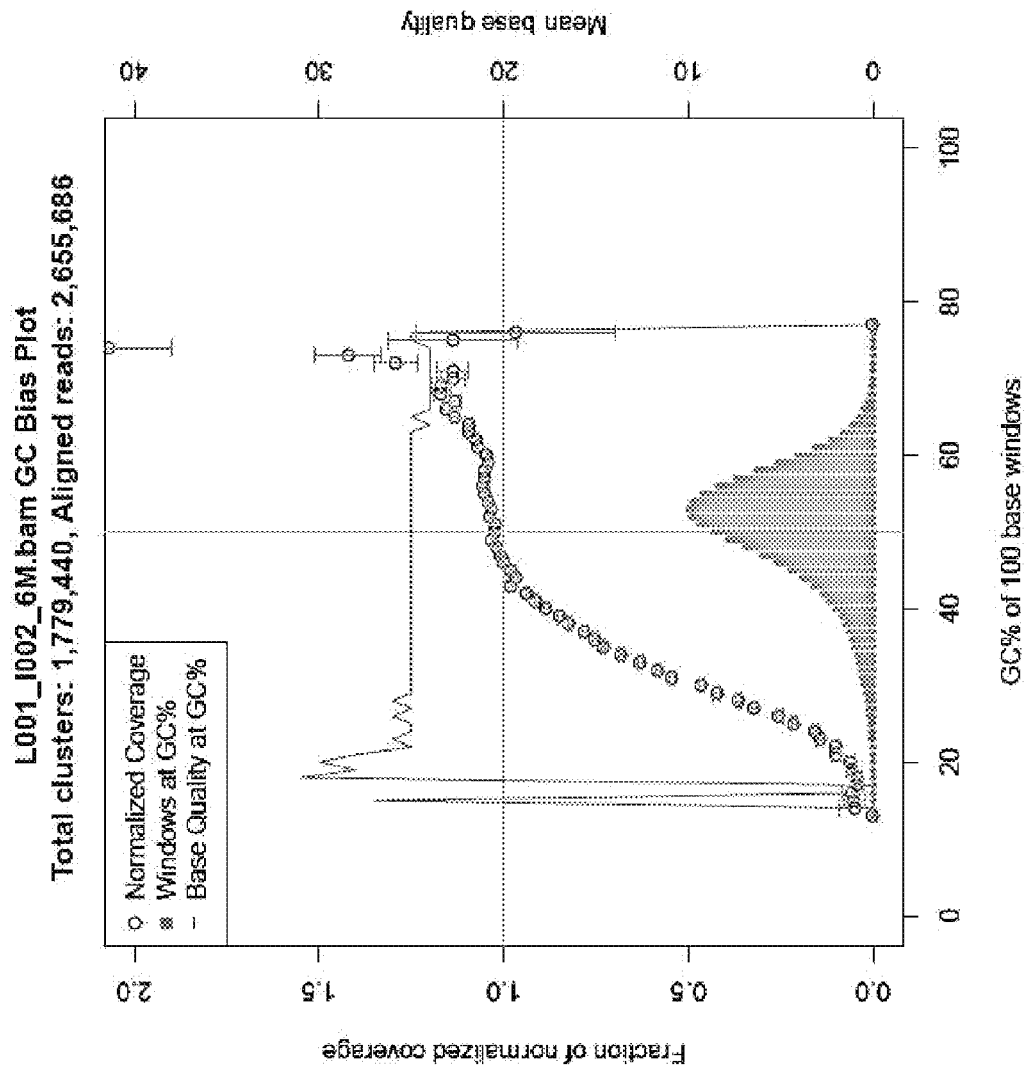

Figure 10, cont.
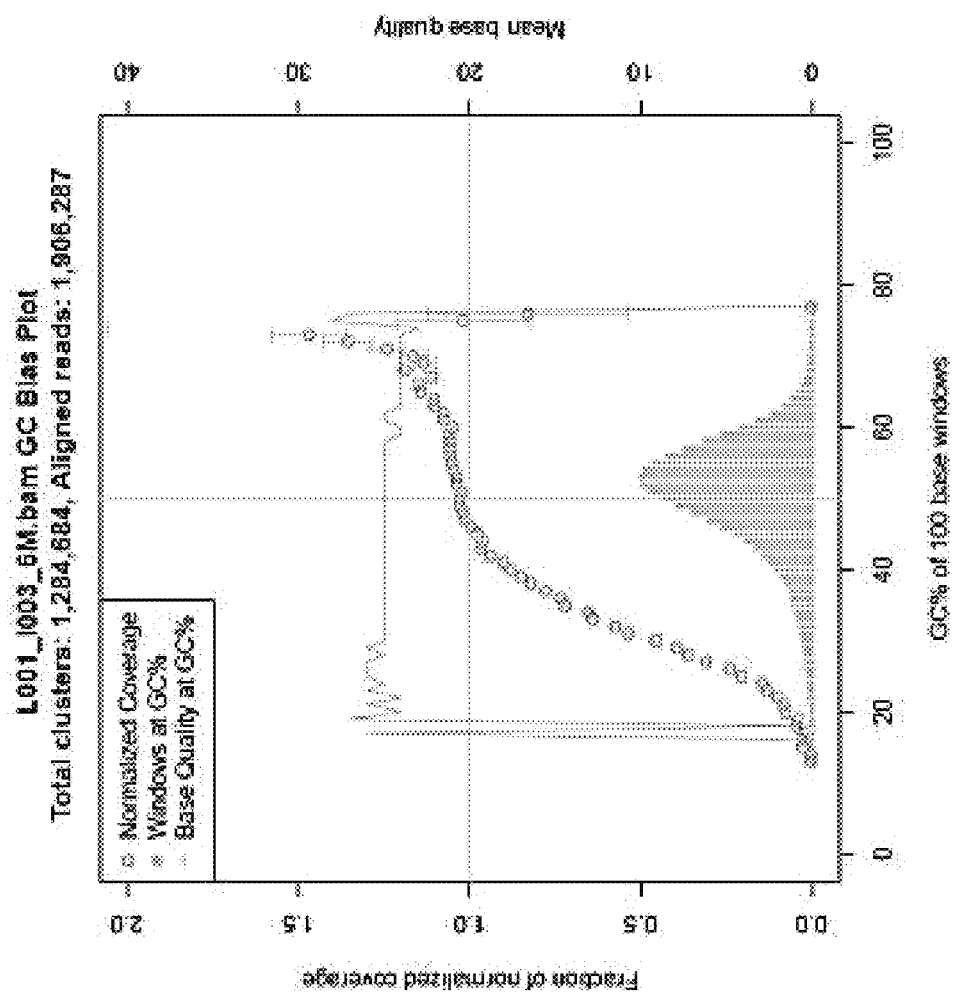

Figure 10, cont.
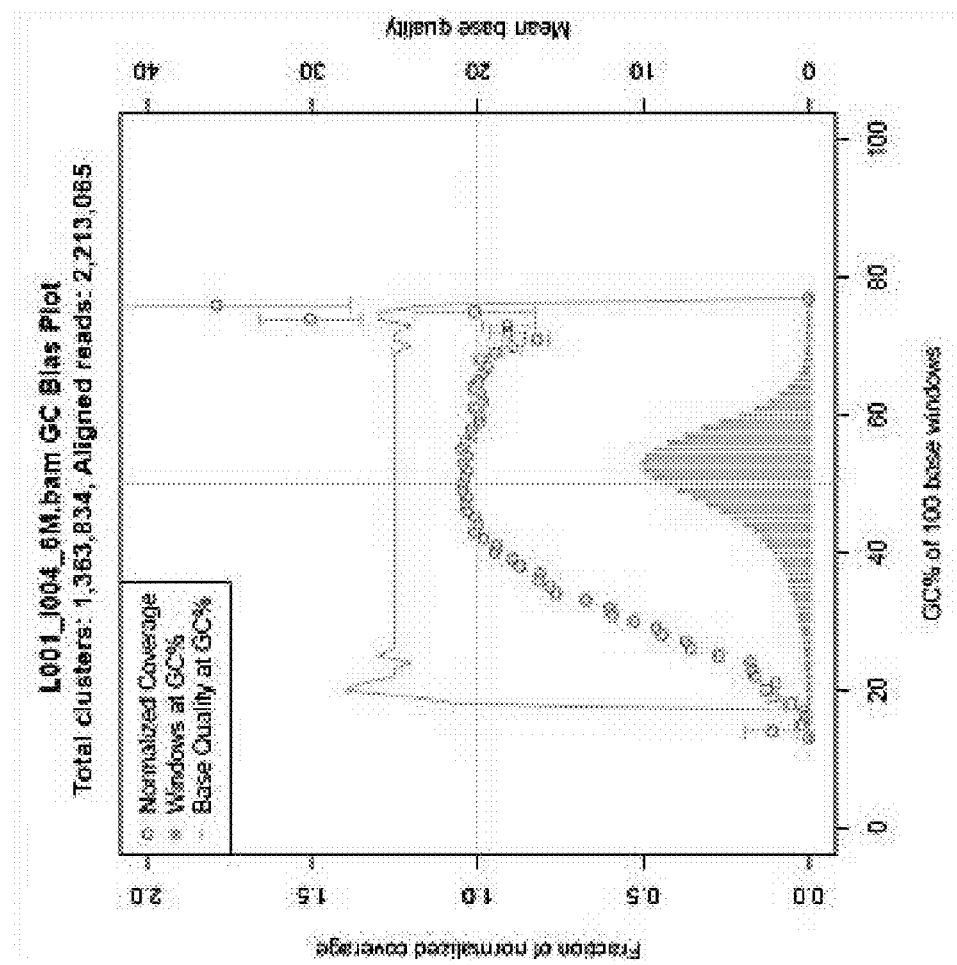

Figure 10, cont.
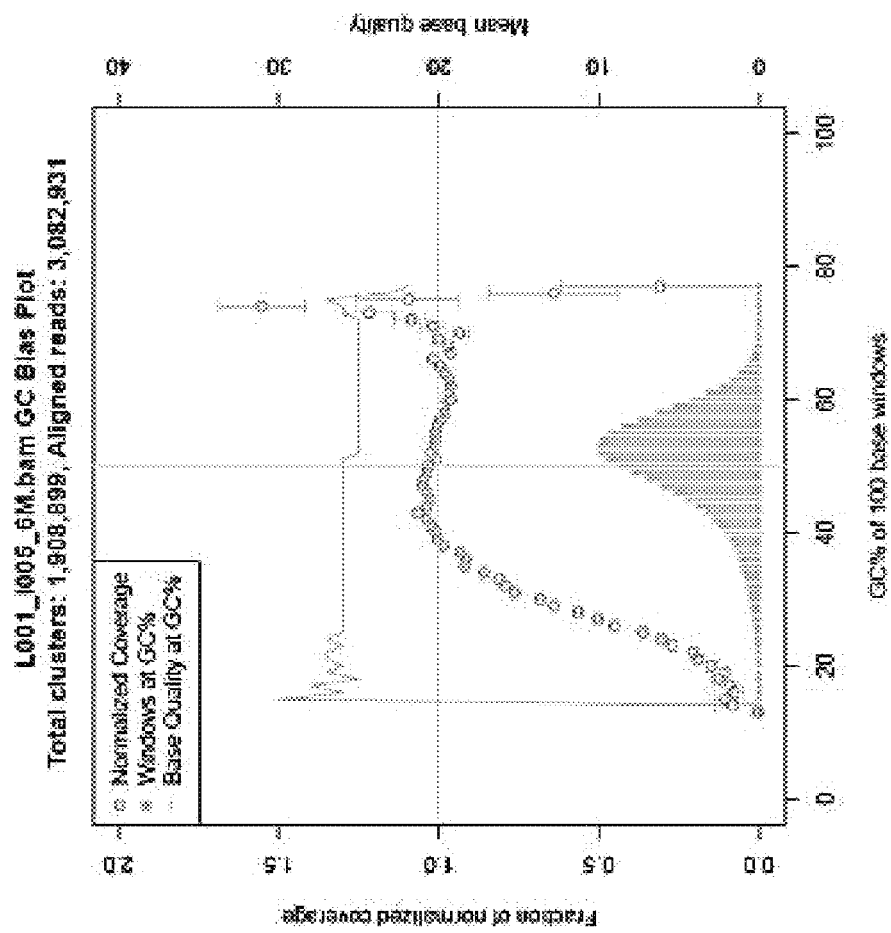
5

Figure 10, cont.
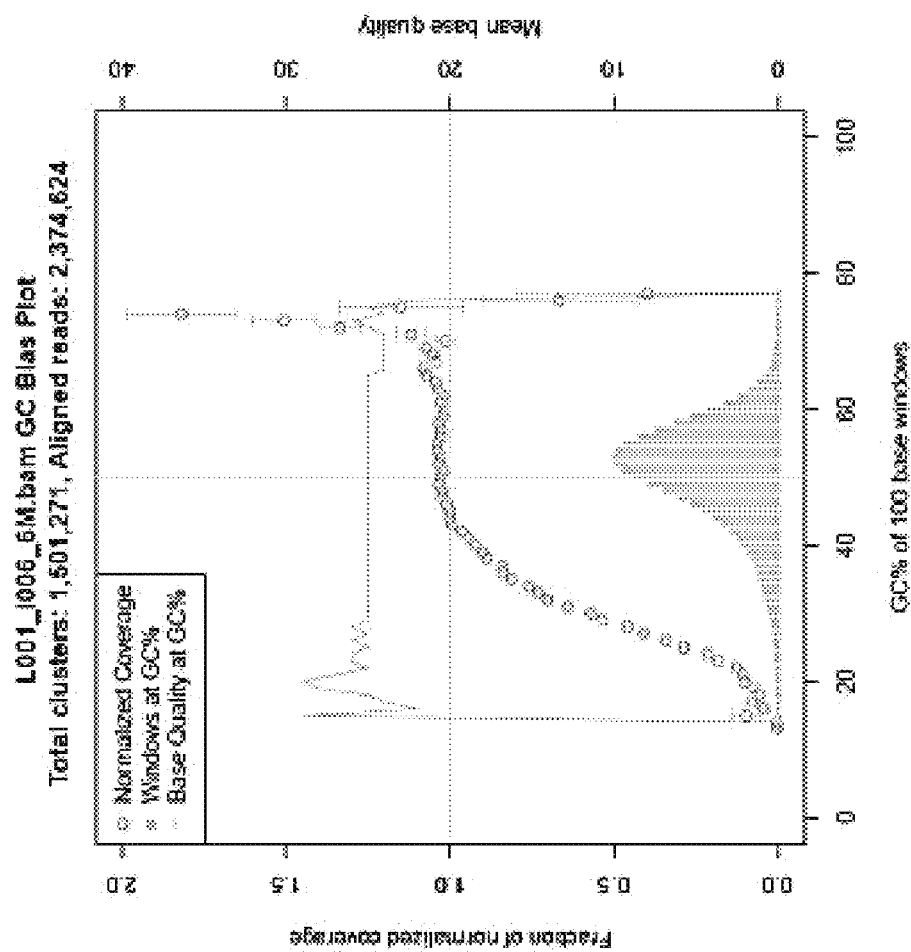

SEQUENCE LISTING

```
<160> NUMBER OF SEQ ID NOS: 42

<210> SEQ ID NO 1
<211> LENGTH: 459
<212> TYPE: PRT
<213> ORGANISM: Vibrio harveyi

<400> SEQUENCE: 1

Met Thr His Ser Asp Ala Lys Leu Trp Ala Gln Glu Gln Phe Gly Gln
1               5                   10                  15

Ala Gln Leu Lys Asp Pro Arg Arg Thr Gln Arg Leu Ile Ser Leu Ala
            20                  25                  30

Thr Ser Ile Ala Asn Gln Pro Gly Val Ser Val Ala Lys Leu Pro Phe
        35                  40                  45

Ser Pro Ala Asp Met Glu Gly Ala Tyr Arg Phe Ile Arg Asn Glu Asn
    50                  55                  60

Ile Asn Ala Glu Asp Ile Ala Glu Ala Gly Phe Gln Ser Thr Val Ser
65                  70                  75                  80

Arg Ala Asn Glu His Lys Glu Leu Leu Ala Leu Glu Asp Thr Thr Thr
                85                  90                  95

Leu Ser Phe Pro His Arg Ser Ile Lys Glu Glu Leu Gly His Thr Asn
            100                 105                 110

Gln Gly Asp Arg Thr Arg Ala Leu His Val His Ser Thr Leu Leu Phe
        115                 120                 125

Ala Pro Gln Ser Gln Thr Ile Val Gly Leu Ile Glu Gln Gln Arg Trp
    130                 135                 140

Ser Arg Asp Ile Thr Lys Arg Gly Gln Lys His Gln His Ala Thr Arg
145                 150                 155                 160

Pro Tyr Lys Glu Lys Glu Ser Tyr Lys Trp Glu Gln Ala Ser Arg Arg
                165                 170                 175

Val Val Glu Arg Leu Gly Asp Lys Met Leu Asp Val Ile Ser Val Cys
            180                 185                 190

Asp Arg Glu Ala Asp Leu Phe Glu Tyr Leu Thr Tyr Lys Arg Gln His
        195                 200                 205
```

```
Gln Gln Arg Phe Val Val Arg Ser Met Gln Ser Arg Cys Leu Glu Glu
    210                 215                 220

His Ala Gln Lys Leu Tyr Asp Tyr Ala Gln Ala Leu Pro Ser Val Glu
225                 230                 235                 240

Thr Lys Ala Leu Thr Ile Pro Gln Lys Gly Gly Arg Lys Ala Arg Asn
                245                 250                 255

Val Lys Leu Asp Val Lys Tyr Gly Gln Val Thr Leu Lys Ala Pro Ala
            260                 265                 270

Asn Lys Lys Glu His Ala Gly Ile Pro Val Tyr Tyr Val Gly Cys Leu
        275                 280                 285

Glu Gln Gly Thr Ser Lys Asp Lys Leu Ala Trp His Leu Leu Thr Ser
    290                 295                 300

Glu Pro Ile Asn Asn Val Asp Asp Ala Met Arg Ile Ile Gly Tyr Tyr
305                 310                 315                 320

Glu Arg Arg Trp Leu Ile Glu Asp Phe His Lys Val Trp Lys Ser Glu
                325                 330                 335

Gly Thr Asp Val Glu Ser Leu Arg Leu Gln Ser Lys Asp Asn Leu Glu
            340                 345                 350

Arg Leu Ser Val Ile Tyr Ala Phe Val Ala Thr Arg Leu Leu Ala Leu
        355                 360                 365

Arg Phe Met Lys Glu Val Asp Glu Leu Thr Lys Glu Ser Cys Glu Lys
    370                 375                 380

Val Leu Gly Gln Lys Ala Trp Lys Leu Leu Trp Leu Lys Leu Glu Ser
385                 390                 395                 400

Lys Thr Leu Pro Lys Glu Val Pro Asp Met Gly Trp Ala Tyr Lys Asn
                405                 410                 415

Leu Ala Lys Leu Gly Gly Trp Lys Asp Thr Lys Arg Thr Gly Arg Ala
            420                 425                 430

Ser Ile Lys Val Leu Trp Glu Gly Trp Phe Lys Leu Gln Thr Ile Leu
        435                 440                 445

Glu Gly Tyr Glu Leu Ala Met Ser Leu Asp His
    450                 455

<210> SEQ ID NO 2
<211> LENGTH: 21
<212> TYPE: PRT
<213> ORGANISM: Artificial Sequence
<220> FEATURE:
<223> OTHER INFORMATION: Artificial sequence added to C-terminus of
      Vibhar sequence

<400> SEQUENCE: 2

Gly Gly Gly Arg Gln Ile Lys Ile Trp Phe Gln Asn Arg Arg Met Lys
1               5                   10                  15

Trp Lys Lys Glu Asn
            20

<210> SEQ ID NO 3
<211> LENGTH: 480
<212> TYPE: PRT
<213> ORGANISM: Artificial Sequence
<220> FEATURE:
<223> OTHER INFORMATION: Vibhar sequence with C-terminal extension of
      SEQ ID NO:2

<400> SEQUENCE: 3

Met Thr His Ser Asp Ala Lys Leu Trp Ala Gln Glu Gln Phe Gly Gln
1               5                   10                  15
```

```
Ala Gln Leu Lys Asp Pro Arg Thr Gln Arg Leu Ile Ser Leu Ala
             20                  25                  30

Thr Ser Ile Ala Asn Gln Pro Gly Val Ser Val Ala Lys Leu Pro Phe
         35                  40                  45

Ser Pro Ala Asp Met Glu Gly Ala Tyr Arg Phe Ile Arg Asn Glu Asn
 50                  55                  60

Ile Asn Ala Glu Asp Ile Ala Glu Ala Gly Phe Gln Ser Thr Val Ser
 65                  70                  75                  80

Arg Ala Asn Glu His Lys Glu Leu Leu Ala Leu Glu Asp Thr Thr Thr
                 85                  90                  95

Leu Ser Phe Pro His Arg Ser Ile Lys Glu Glu Leu Gly His Thr Asn
            100                 105                 110

Gln Gly Asp Arg Thr Arg Ala Leu His Val His Ser Thr Leu Leu Phe
        115                 120                 125

Ala Pro Gln Ser Gln Thr Ile Val Gly Leu Ile Glu Gln Gln Arg Trp
130                 135                 140

Ser Arg Asp Ile Thr Lys Arg Gly Gln Lys His Gln His Ala Thr Arg
145                 150                 155                 160

Pro Tyr Lys Glu Lys Glu Ser Tyr Lys Trp Glu Gln Ala Ser Arg Arg
                165                 170                 175

Val Val Glu Arg Leu Gly Asp Lys Met Leu Asp Val Ile Ser Val Cys
            180                 185                 190

Asp Arg Glu Ala Asp Leu Phe Glu Tyr Leu Thr Tyr Lys Arg Gln His
        195                 200                 205

Gln Gln Arg Phe Val Val Arg Ser Met Gln Ser Arg Cys Leu Glu Glu
    210                 215                 220

His Ala Gln Lys Leu Tyr Asp Tyr Ala Gln Ala Leu Pro Ser Val Glu
225                 230                 235                 240

Thr Lys Ala Leu Thr Ile Pro Gln Lys Gly Gly Arg Lys Ala Arg Asn
                245                 250                 255

Val Lys Leu Asp Val Lys Tyr Gly Gln Val Thr Leu Lys Ala Pro Ala
            260                 265                 270

Asn Lys Lys Glu His Ala Gly Ile Pro Val Tyr Val Gly Cys Leu
        275                 280                 285

Glu Gln Gly Thr Ser Lys Asp Lys Leu Ala Trp His Leu Leu Thr Ser
    290                 295                 300

Glu Pro Ile Asn Asn Val Asp Asp Ala Met Arg Ile Ile Gly Tyr Tyr
305                 310                 315                 320

Glu Arg Arg Trp Leu Ile Glu Asp Phe His Lys Val Trp Lys Ser Glu
                325                 330                 335

Gly Thr Asp Val Glu Ser Leu Arg Leu Gln Ser Lys Asp Asn Leu Glu
            340                 345                 350

Arg Leu Ser Val Ile Tyr Ala Phe Val Ala Thr Arg Leu Leu Ala Leu
        355                 360                 365

Arg Phe Met Lys Glu Val Asp Glu Leu Thr Lys Glu Ser Cys Glu Lys
    370                 375                 380

Val Leu Gly Gln Lys Ala Trp Lys Leu Leu Trp Leu Lys Leu Glu Ser
385                 390                 395                 400

Lys Thr Leu Pro Lys Glu Val Pro Asp Met Gly Trp Ala Tyr Lys Asn
                405                 410                 415

Leu Ala Lys Leu Gly Gly Trp Lys Asp Thr Lys Arg Thr Gly Arg Ala
            420                 425                 430
```

-continued

```
Ser Ile Lys Val Leu Trp Glu Gly Trp Phe Lys Leu Gln Thr Ile Leu
            435                 440                 445

Glu Gly Tyr Glu Leu Ala Met Ser Leu Asp His Gly Gly Arg Gln
    450                 455                 460

Ile Lys Ile Trp Phe Gln Asn Arg Arg Met Lys Trp Lys Lys Glu Asn
465                 470                 475                 480

<210> SEQ ID NO 4
<211> LENGTH: 11
<212> TYPE: PRT
<213> ORGANISM: Artificial Sequence
<220> FEATURE:
<223> OTHER INFORMATION: Artificial sequence added to C-terminus of
      Vibhar sequence

<400> SEQUENCE: 4

Gly Gly Gly Lys Lys Arg Lys Arg Glu Arg
1               5                   10

<210> SEQ ID NO 5
<211> LENGTH: 470
<212> TYPE: PRT
<213> ORGANISM: Artificial Sequence
<220> FEATURE:
<223> OTHER INFORMATION: Full length sequence of Vibhar plus SEQ ID NO:4

<400> SEQUENCE: 5

Met Thr His Ser Asp Ala Lys Leu Trp Ala Gln Glu Gln Phe Gly Gln
1               5                   10                  15

Ala Gln Leu Lys Asp Pro Arg Arg Thr Gln Arg Leu Ile Ser Leu Ala
            20                  25                  30

Thr Ser Ile Ala Asn Gln Pro Gly Val Ser Val Ala Lys Leu Pro Phe
        35                  40                  45

Ser Pro Ala Asp Met Glu Gly Ala Tyr Arg Phe Ile Arg Asn Glu Asn
    50                  55                  60

Ile Asn Ala Glu Asp Ile Ala Glu Ala Gly Phe Gln Ser Thr Val Ser
65                  70                  75                  80

Arg Ala Asn Glu His Lys Glu Leu Leu Ala Leu Glu Asp Thr Thr Thr
                85                  90                  95

Leu Ser Phe Pro His Arg Ser Ile Lys Glu Glu Leu Gly His Thr Asn
            100                 105                 110

Gln Gly Asp Arg Thr Arg Ala Leu His Val His Ser Thr Leu Leu Phe
        115                 120                 125

Ala Pro Gln Ser Gln Thr Ile Val Gly Leu Ile Glu Gln Gln Arg Trp
    130                 135                 140

Ser Arg Asp Ile Thr Lys Arg Gly Gln Lys His Gln His Ala Thr Arg
145                 150                 155                 160

Pro Tyr Lys Glu Lys Glu Ser Tyr Lys Trp Glu Gln Ala Ser Arg Arg
                165                 170                 175

Val Val Glu Arg Leu Gly Asp Lys Met Leu Asp Val Ile Ser Val Cys
            180                 185                 190

Asp Arg Glu Ala Asp Leu Phe Glu Tyr Leu Thr Tyr Lys Arg Gln His
        195                 200                 205

Gln Gln Arg Phe Val Val Arg Ser Met Gln Ser Arg Cys Leu Glu Glu
    210                 215                 220

His Ala Gln Lys Leu Tyr Asp Tyr Ala Gln Ala Leu Pro Ser Val Glu
225                 230                 235                 240

Thr Lys Ala Leu Thr Ile Pro Gln Lys Gly Gly Arg Lys Ala Arg Asn
```

```
                245                 250                 255
Val Lys Leu Asp Val Lys Tyr Gly Gln Val Thr Leu Lys Ala Pro Ala
            260                 265                 270

Asn Lys Lys Glu His Ala Gly Ile Pro Val Tyr Tyr Val Gly Cys Leu
        275                 280                 285

Glu Gln Gly Thr Ser Lys Asp Lys Leu Ala Trp His Leu Leu Thr Ser
    290                 295                 300

Glu Pro Ile Asn Asn Val Asp Asp Ala Met Arg Ile Ile Gly Tyr Tyr
305                 310                 315                 320

Glu Arg Arg Trp Leu Ile Glu Asp Phe His Lys Val Trp Lys Ser Glu
                325                 330                 335

Gly Thr Asp Val Glu Ser Leu Arg Leu Gln Ser Lys Asp Asn Leu Glu
            340                 345                 350

Arg Leu Ser Val Ile Tyr Ala Phe Val Ala Thr Arg Leu Leu Ala Leu
        355                 360                 365

Arg Phe Met Lys Glu Val Asp Glu Leu Thr Lys Glu Ser Cys Glu Lys
    370                 375                 380

Val Leu Gly Gln Lys Ala Trp Lys Leu Leu Trp Leu Lys Leu Glu Ser
385                 390                 395                 400

Lys Thr Leu Pro Lys Glu Val Pro Asp Met Gly Trp Ala Tyr Lys Asn
                405                 410                 415

Leu Ala Lys Leu Gly Gly Trp Lys Asp Thr Lys Arg Thr Gly Arg Ala
            420                 425                 430

Ser Ile Lys Val Leu Trp Glu Gly Trp Phe Lys Leu Gln Thr Ile Leu
        435                 440                 445

Glu Gly Tyr Glu Leu Ala Met Ser Leu Asp His Gly Gly Gly Lys Lys
    450                 455                 460

Lys Arg Lys Arg Glu Arg
465                 470

<210> SEQ ID NO 6
<211> LENGTH: 12
<212> TYPE: PRT
<213> ORGANISM: Artificial Sequence
<220> FEATURE:
<223> OTHER INFORMATION: Artificial sequence for addition to Vibhar C-
      terminus

<400> SEQUENCE: 6

Gly Gly Gly Lys Tyr Arg Pro Arg Arg Lys Gln
1               5                   10

<210> SEQ ID NO 7
<211> LENGTH: 471
<212> TYPE: PRT
<213> ORGANISM: Artificial Sequence
<220> FEATURE:
<223> OTHER INFORMATION: Full length sequence of Vibhar plus SEQ ID NO:6

<400> SEQUENCE: 7

Met Thr His Ser Asp Ala Lys Leu Trp Ala Gln Glu Gln Phe Gly Gln
1               5                   10                  15

Ala Gln Leu Lys Asp Pro Arg Arg Thr Gln Arg Leu Ile Ser Leu Ala
            20                  25                  30

Thr Ser Ile Ala Asn Gln Pro Gly Val Ser Val Ala Lys Leu Pro Phe
        35                  40                  45

Ser Pro Ala Asp Met Glu Gly Ala Tyr Arg Phe Ile Arg Asn Glu Asn
    50                  55                  60
```

```
Ile Asn Ala Glu Asp Ile Ala Glu Ala Gly Phe Gln Ser Thr Val Ser
 65                  70                  75                  80

Arg Ala Asn Glu His Lys Glu Leu Leu Ala Leu Glu Asp Thr Thr Thr
                 85                  90                  95

Leu Ser Phe Pro His Arg Ser Ile Lys Glu Glu Leu Gly His Thr Asn
            100                 105                 110

Gln Gly Asp Arg Thr Arg Ala Leu His Val His Ser Thr Leu Leu Phe
        115                 120                 125

Ala Pro Gln Ser Gln Thr Ile Val Gly Leu Ile Glu Gln Gln Arg Trp
    130                 135                 140

Ser Arg Asp Ile Thr Lys Arg Gly Gln Lys His Gln His Ala Thr Arg
145                 150                 155                 160

Pro Tyr Lys Glu Lys Glu Ser Tyr Lys Trp Glu Gln Ala Ser Arg Arg
                165                 170                 175

Val Val Glu Arg Leu Gly Asp Lys Met Leu Asp Val Ile Ser Val Cys
            180                 185                 190

Asp Arg Glu Ala Asp Leu Phe Glu Tyr Leu Thr Tyr Lys Arg Gln His
        195                 200                 205

Gln Gln Arg Phe Val Val Arg Ser Met Gln Ser Arg Cys Leu Glu Glu
    210                 215                 220

His Ala Gln Lys Leu Tyr Asp Tyr Ala Gln Ala Leu Pro Ser Val Glu
225                 230                 235                 240

Thr Lys Ala Leu Thr Ile Pro Gln Lys Gly Gly Arg Lys Ala Arg Asn
                245                 250                 255

Val Lys Leu Asp Val Lys Tyr Gly Gln Val Thr Leu Lys Ala Pro Ala
            260                 265                 270

Asn Lys Lys Glu His Ala Gly Ile Pro Val Tyr Tyr Val Gly Cys Leu
        275                 280                 285

Glu Gln Gly Thr Ser Lys Asp Lys Leu Ala Trp His Leu Leu Thr Ser
    290                 295                 300

Glu Pro Ile Asn Asn Val Asp Asp Ala Met Arg Ile Ile Gly Tyr Tyr
305                 310                 315                 320

Glu Arg Arg Trp Leu Ile Glu Asp Phe His Lys Val Trp Lys Ser Glu
                325                 330                 335

Gly Thr Asp Val Glu Ser Leu Arg Leu Gln Ser Lys Asp Asn Leu Glu
            340                 345                 350

Arg Leu Ser Val Ile Tyr Ala Phe Val Ala Thr Arg Leu Leu Ala Leu
        355                 360                 365

Arg Phe Met Lys Glu Val Asp Glu Leu Thr Lys Glu Ser Cys Glu Lys
    370                 375                 380

Val Leu Gly Gln Lys Ala Trp Lys Leu Leu Trp Leu Lys Leu Glu Ser
385                 390                 395                 400

Lys Thr Leu Pro Lys Glu Val Pro Asp Met Gly Trp Ala Tyr Lys Asn
                405                 410                 415

Leu Ala Lys Leu Gly Gly Trp Lys Asp Thr Lys Arg Thr Gly Arg Ala
            420                 425                 430

Ser Ile Lys Val Leu Trp Glu Gly Trp Phe Lys Leu Gln Thr Ile Leu
        435                 440                 445

Glu Gly Tyr Glu Leu Ala Met Ser Leu Asp His Gly Gly Lys Tyr
    450                 455                 460

Arg Pro Arg Arg Arg Lys Gln
465                 470
```

<210> SEQ ID NO 8
<211> LENGTH: 461
<212> TYPE: PRT
<213> ORGANISM: Photobacterium profundum

<400> SEQUENCE: 8

```
Met Tyr Ile Ser Thr Pro Gln Asp Trp Ala Thr Ser Leu Phe Gly Gln
1               5                   10                  15

Ala Asn Leu Gly Asp Pro Arg Arg Thr Lys Arg Leu Val Lys Val Ala
            20                  25                  30

Thr Asn Leu Ala Leu His Thr Gly Gly Ser Leu Val Lys Ser Ser Gln
        35                  40                  45

Gln Pro Ala Glu Ile Glu Gly Ala Tyr Arg Phe Ile Arg Asn Glu Ser
    50                  55                  60

Ile Asn Ala Asn Asp Ile Ala Glu Ala Gly Phe Gln Thr Thr Thr Gln
65                  70                  75                  80

Glu Ala Asn Arg His Asp Leu Leu Ala Leu Glu Asp Thr Thr Ser
                85                  90                  95

Leu Asn Tyr Thr His Arg Ala Val Lys Glu Gln Leu Gly His Val Asn
            100                 105                 110

Gly Gly Asn Arg Thr Arg Gly Ile Tyr Ala His Ser Ile Leu Leu Phe
        115                 120                 125

Ala Pro Thr Asn His Gln Val Val Gly Leu Ile Glu Gln Ile Arg Trp
    130                 135                 140

Thr Arg Asp Ile Lys Thr Arg Gly Lys Gly Ala Arg His Ala Gln Thr
145                 150                 155                 160

Pro Tyr Lys Glu Lys Glu Ser Tyr Lys Trp Glu Gln Ala Ser Ile Asn
                165                 170                 175

Met Ala Ser Arg Leu Gly Glu Thr Met Gln Gln Val Ile Ser Val Cys
            180                 185                 190

Asp Arg Glu Ala Asp Ile Tyr Glu Tyr Leu Thr Tyr Lys Thr Gln Glu
        195                 200                 205

Asn Gln Arg Phe Val Val Arg Ser Met Gln Ser Arg Cys Ile Glu Glu
    210                 215                 220

Ser Asp Asn Lys Leu Tyr Ala Phe Ser Asp Gln Leu Gln Pro Ala Gly
225                 230                 235                 240

Asn Arg Lys Ile Tyr Ile Pro Gln Lys Gly Arg Lys Ala Arg Glu
                245                 250                 255

Val Ile Leu Asp Ile Arg Phe Ser Thr Ile Thr Leu Lys Val Pro Ala
            260                 265                 270

Asn Lys Lys Gly Lys Ser Ile Pro Leu Tyr Tyr Val Gly Cys Val Glu
        275                 280                 285

Gln Gly Ala Gly Asp Asn Gly Leu Ser Trp His Leu Met Thr Ser Glu
    290                 295                 300

Pro Val Thr Asn Arg Glu Glu Ala Leu Lys Ile Val Gln Tyr Tyr Glu
305                 310                 315                 320

Gln Arg Trp Leu Ile Glu Asp Tyr His Lys Ala Trp Lys Ser Gly Gly
                325                 330                 335

Thr Gln Val Glu Ser Leu Arg Met Gln Ser Tyr Thr Asn Ile Glu Arg
            340                 345                 350

Met Ala Thr Ile Leu Ala Phe Leu Ala Ala Arg Ile Leu Gln Leu Lys
        355                 360                 365

Phe Met Gly Gln Asn Ile Lys Ala Asp Glu Glu Ser Cys Glu Ser Val
    370                 375                 380
```

```
Leu Ser Pro Ile Gly Trp Lys Leu Leu Trp Leu Lys Arg Glu Asn Lys
385                 390                 395                 400

Pro Leu Pro Asn Glu Val Pro Ser Ile Arg Trp Ala Tyr Leu Ala Leu
                405                 410                 415

Ala Lys Leu Gly Gly Trp Asn Asp Ser Lys Arg Thr Gly Arg Ala Gly
            420                 425                 430

Trp Pro Val Leu Trp Asp Gly Trp Phe Lys Leu Gln Thr Ile Ile Glu
        435                 440                 445

Gly Tyr His Leu Ala Gln Ser Leu Glu Cys Leu Asp Leu
    450                 455                 460

<210> SEQ ID NO 9
<211> LENGTH: 462
<212> TYPE: PRT
<213> ORGANISM: Artificial Sequence
<220> FEATURE:
<223> OTHER INFORMATION: Chimeric sequence of Vibhar and P. profundum

<400> SEQUENCE: 9

Met Thr His Ser Asp Ala Lys Leu Trp Ala Gln Glu Gln Phe Gly Gln
1               5                   10                  15

Ala Gln Leu Lys Asp Pro Arg Arg Thr Gln Arg Leu Ile Ser Leu Ala
            20                  25                  30

Thr Ser Ile Ala Asn Gln Pro Gly Val Ser Val Ala Lys Leu Pro Phe
        35                  40                  45

Ser Pro Ala Asp Met Glu Gly Ala Tyr Arg Phe Ile Arg Asn Glu Asn
    50                  55                  60

Ile Asn Ala Glu Asp Ile Ala Glu Ala Gly Phe Gln Ser Thr Val Ser
65                  70                  75                  80

Arg Ala Asn Glu His Lys Glu Leu Leu Ala Leu Glu Asp Thr Thr Thr
                85                  90                  95

Leu Ser Phe Pro His Arg Ser Ile Lys Glu Glu Leu Gly His Thr Asn
            100                 105                 110

Gln Gly Asp Arg Thr Arg Ala Leu His Val His Ser Thr Leu Leu Phe
        115                 120                 125

Ala Pro Gln Ser Gln Thr Ile Val Gly Leu Ile Glu Gln Gln Arg Trp
    130                 135                 140

Ser Arg Asp Ile Thr Lys Arg Gly Gln Lys His Gln His Ala Thr Arg
145                 150                 155                 160

Pro Tyr Lys Glu Lys Glu Ser Tyr Lys Trp Glu Gln Ala Ser Arg Arg
                165                 170                 175

Val Val Glu Arg Leu Gly Asp Lys Met Leu Asp Val Ile Ser Val Cys
            180                 185                 190

Asp Arg Glu Ala Asp Leu Phe Glu Tyr Leu Thr Tyr Lys Arg Gln His
        195                 200                 205

Gln Gln Arg Phe Val Val Arg Ser Met Gln Ser Arg Cys Leu Glu Glu
    210                 215                 220

His Ala Gln Lys Leu Tyr Asp Tyr Ala Gln Ala Leu Pro Ser Val Glu
225                 230                 235                 240

Thr Lys Ala Leu Thr Ile Pro Gln Lys Gly Gly Arg Lys Ala Arg Asn
                245                 250                 255

Val Lys Leu Asp Val Lys Tyr Gly Gln Val Thr Leu Lys Ala Pro Ala
            260                 265                 270

Asn Lys Lys Glu His Ala Gly Ile Pro Val Tyr Tyr Val Gly Cys Leu
        275                 280                 285
```

```
Glu Gln Gly Thr Ser Lys Asp Lys Leu Ala Trp His Leu Leu Thr Ser
        290                 295                 300
Glu Pro Ile Asn Asn Val Asp Asp Ala Met Arg Ile Ile Gly Tyr Tyr
305                 310                 315                 320
Glu Arg Arg Trp Leu Ile Glu Asp Phe His Lys Val Trp Lys Ser Glu
                325                 330                 335
Gly Thr Asp Val Glu Ser Leu Arg Leu Gln Ser Lys Asp Asn Leu Glu
                340                 345                 350
Arg Leu Ser Val Ile Tyr Ala Phe Val Ala Thr Arg Leu Leu Ala Leu
                355                 360                 365
Lys Phe Met Gly Gln Asn Ile Lys Ala Asp Glu Glu Ser Cys Glu Ser
        370                 375                 380
Val Leu Ser Pro Ile Gly Trp Lys Leu Leu Trp Leu Lys Arg Glu Asn
385                 390                 395                 400
Lys Pro Leu Pro Asn Glu Val Pro Ser Ile Arg Trp Ala Tyr Leu Ala
                405                 410                 415
Leu Ala Lys Leu Gly Gly Trp Asn Asp Ser Lys Arg Thr Gly Arg Ala
                420                 425                 430
Gly Trp Pro Val Leu Trp Asp Gly Trp Phe Lys Leu Gln Thr Ile Ile
                435                 440                 445
Glu Gly Tyr His Leu Ala Gln Ser Leu Glu Cys Leu Asp Leu
        450                 455                 460

<210> SEQ ID NO 10
<211> LENGTH: 465
<212> TYPE: PRT
<213> ORGANISM: Vibrio cholera

<400> SEQUENCE: 10

Met Ile Arg Met Thr Tyr Ile Glu Pro Thr Leu Trp Ala Gln Lys Gln
1               5                   10                  15
Phe Gly Gln Ala His Leu Asn Asp Pro Arg Arg Thr Gln Arg Leu Val
                20                  25                  30
Ala Leu Ala Ala Ser Leu Ala Glu Gln Pro Gly Val Pro Val Ser Lys
        35                  40                  45
Leu Ile Ile Ser Pro Ala Asp Met Glu Gly Ala Tyr Arg Phe Ile Arg
50                  55                  60
Asn Glu Gln Ile Lys Ala Glu Asp Ile Ala Glu Ala Gly Phe His Val
65                  70                  75                  80
Thr Ala Gln Glu Ala Leu Glu Gln Gln Thr Leu Leu Ala Leu Glu Asp
                85                  90                  95
Thr Thr Ser Leu Ser Tyr Ser His Arg Ser Ile Gln Asp Glu Leu Gly
                100                 105                 110
His Ser Asn Gln Gly Asn Arg Asn Arg Ala Met Phe Ile His Ser Thr
        115                 120                 125
Leu Leu Phe Ala Pro Glu Thr Gln Val Val Gly Leu Ile Glu Gln
        130                 135                 140
Gln Arg Trp Thr Arg Asp Ile Glu Lys Arg Gly Gln Gly His Gln Tyr
145                 150                 155                 160
Ala Thr Arg Pro Tyr Lys Glu Lys Glu Ser Tyr Lys Trp Glu Gln Ala
                165                 170                 175
Ser Arg His Val Ala Glu Arg Leu Gly Asp Lys Ile Ser Asp Val Ile
                180                 185                 190
Ser Val Cys Asp Arg Glu Ala Asp Leu Phe Glu Tyr Leu Thr Tyr Lys
```

```
                     195                 200                 205
Gln Glu Gln Gln Gln Arg Phe Leu Val Arg Ser Met Gln Ser Arg Cys
    210                 215                 220

Ile Glu Glu His Asp Asn Arg Leu Tyr Asp Tyr Ala Ser Lys Leu Gln
225                 230                 235                 240

Ser Ala Gly Glu Arg Val Leu Asp Ile Pro Gln Lys Gly Gly Arg Lys
                245                 250                 255

Ala Arg Thr Val His Leu Asp Ile Lys Tyr Ala Pro Val Thr Leu Lys
            260                 265                 270

Ser Pro Ala Asn Lys Lys Glu Phe Asn Asn Ile Pro Leu Tyr Tyr Val
        275                 280                 285

Gly Cys Ile Glu Gln Gly Ser Asn Asp Lys Leu Ala Trp His Leu
    290                 295                 300

Leu Thr Ser Glu Pro Ile Thr Ser Lys Glu Glu Ala Leu Lys Ile Val
305                 310                 315                 320

Ser Tyr Tyr Glu Leu Arg Trp Leu Ile Glu Asp Phe His Lys Val Trp
                325                 330                 335

Lys Ser Glu Gly Thr Gln Val Glu Gln Leu Arg Met Gln Ser Lys Asp
            340                 345                 350

Asn Leu Glu Arg Leu Ser Val Ile Leu Ala Phe Ile Ala Thr Arg Leu
        355                 360                 365

Leu Gln Leu Arg Phe Met Asn Glu Ser Asp Glu Leu Ser Lys Ser Ser
    370                 375                 380

Cys Glu Pro Ile Leu Lys Gly Lys Ala Trp Lys Leu Met Trp Leu Lys
385                 390                 395                 400

Leu Glu Arg Lys Gly Leu Pro Lys Glu Ala Pro Asp Ile Ser Trp Ala
                405                 410                 415

Tyr Lys Gly Ile Ala Arg Leu Gly Trp Lys Asn Thr Lys Arg Thr
            420                 425                 430

Gly Arg Ala Ser Ile Lys Thr Leu Trp Gln Gly Trp Phe Arg Leu Gln
        435                 440                 445

Thr Ile Leu Glu Gly Tyr Glu Leu Ala Lys Ser Leu Asp Ser Pro Asp
    450                 455                 460

Leu
465

<210> SEQ ID NO 11
<211> LENGTH: 465
<212> TYPE: PRT
<213> ORGANISM: Artificial Sequence
<220> FEATURE:
<223> OTHER INFORMATION: Full length chimeric sequence of V. cholera V51
      t

```
Thr Ala Gln Glu Ala Leu Glu Gln Gln Thr Leu Leu Ala Leu Glu Asp
            85                  90                  95

Thr Thr Ser Leu Ser Tyr Ser His Arg Ser Ile Gln Asp Glu Leu Gly
        100                 105                 110

His Ser Asn Gln Gly Asn Arg Asn Arg Ala Met Phe Ile His Ser Thr
        115                 120                 125

Leu Leu Phe Ala Pro Glu Thr Gln Val Val Gly Leu Ile Glu Gln
    130                 135                 140

Gln Arg Trp Thr Arg Asp Ile Lys Lys Arg Gly Gln Arg His Gln His
145                 150                 155                 160

Ala Thr Arg Pro Tyr Lys Glu Lys Glu Ser Tyr Lys Trp Gln Ala
                165                 170                 175

Ser Glu Arg Val Ala Glu Arg Leu Gly Asp Lys Met Ser Asp Val Ile
            180                 185                 190

Ser Val Cys Asp Arg Glu Ala Asp Leu Phe Glu Tyr Leu Thr Tyr Lys
        195                 200                 205

Gln Glu Gln Gln Arg Phe Leu Val Arg Ser Met Gln Ser Arg Cys
    210                 215                 220

Ile Glu Glu His Asp Asn Arg Leu Tyr Asp Tyr Ala Ser Lys Leu Gln
225                 230                 235                 240

Ser Ala Gly Glu Arg Val Leu Asp Ile Pro Gln Lys Gly Arg Lys
                245                 250                 255

Ala Arg Thr Val His Leu Asp Ile Lys Tyr Ala Pro Val Thr Leu Lys
            260                 265                 270

Ser Pro Ala Thr Lys Lys Glu Phe Asn Asn Ile Pro Leu Tyr Tyr Val
        275                 280                 285

Gly Cys Ile Glu Gln Gly Glu Ser Asn Asp Lys Leu Ala Trp His Leu
    290                 295                 300

Leu Thr Ser Glu Pro Ile Thr Ser Lys Glu Glu Ala Leu Lys Ile Val
305                 310                 315                 320

Ser Tyr Tyr Glu Met Arg Trp Leu Ile Glu Asp Phe His Lys Val Trp
                325                 330                 335

Lys Ser Glu Gly Thr Gln Val Glu Gln Leu Arg Met Gln Ser Lys Asp
            340                 345                 350

Asn Leu Glu Arg Leu Ser Val Ile Leu Ala Phe Ile Ala Thr Arg Leu
        355                 360                 365

Leu Gln Leu Arg Phe Met Asn Glu Ser Asp Glu Leu Ser Lys Ser Ser
    370                 375                 380

Cys Glu Arg Ile Leu Lys Gly Lys Ala Trp Lys Leu Met Trp Leu Lys
385                 390                 395                 400

Leu Glu Arg Lys Gly Leu Pro Lys Glu Ala Pro Asp Ile Ser Trp Ala
                405                 410                 415

Tyr Lys Gly Ile Ala Arg Leu Gly Gly Trp Lys Asp Ser Lys Arg Thr
            420                 425                 430

Gly Arg Ala Ser Ile Lys Val Leu Trp Gln Gly Trp Phe Arg Leu Gln
        435                 440                 445

Thr Ile Leu Glu Gly Tyr Glu Leu Ala Lys Ser Leu Asp Gln Leu Asp
    450                 455                 460

Leu
465

<210> SEQ ID NO 12
<211> LENGTH: 465
<212> TYPE: PRT
```

<213> ORGANISM: Artificial Sequence
<220> FEATURE:
<223> OTHER INFORMATION: Full length sequence of Vibhar and Legionella
      pneumophila subsp. pneumophila str. Philadelphia 1 chimeric
      transposase

<400> SEQUENCE: 12

```
Met Thr His Ser Asp Ala Lys Leu Tr

```
Thr Ser Cys Asp Glu Leu Leu Thr Asp Ala Glu Trp Lys Val Leu Trp
385                 390                 395                 400

Asn Ser Val Glu Arg Lys Ser Leu Pro Glu Lys Ile Pro Thr Ala Ala
                405                 410                 415

Trp Ala Tyr Lys Ala Ile Ala Lys Leu Gly Gly Trp Thr Asp Ser Lys
            420                 425                 430

Arg Thr Gly Lys Ala Ala Trp Ser Thr Ile Trp Lys Gly Trp Phe Arg
        435                 440                 445

Leu Gln Glu Arg Val Glu Gly Leu Arg Ile Ala Asn Glu Leu Met Glu
    450                 455                 460

Met
465

<210> SEQ ID NO 13
<211> LENGTH: 462
<212> TYPE: PRT
<213> ORGANISM: Artificial Sequence
<220> FEATURE:
<223> OTHER INFORMATION: Full length sequence of chimeric tranposase of
      Vibhar and Vibrio cholera

<400> SEQUENCE: 13

Met Thr His Ser Asp Ala Lys Leu Trp Ala Gln Glu Gln Phe Gly Gln
1               5                   10                  15

Ala Gln Leu Lys Asp Pro Arg Arg Thr Gln Arg Leu Ile Ser Leu Ala
            20                  25                  30

Thr Ser Ile Ala Asn Gln Pro Gly Val Ser Val Ala Lys Leu Pro Phe
        35                  40                  45

Ser Pro Ala Asp Met Glu Gly Ala Tyr Arg Phe Ile Arg Asn Glu Asn
    50                  55                  60

Ile Asn Ala Glu Asp Ile Ala Glu Ala Gly Phe Gln Ser Thr Val Ser
65              70                  75                  80

Arg Ala Asn Glu His Lys Glu Leu Leu Ala Leu Glu Asp Thr Thr Thr
                85                  90                  95

Leu Ser Phe Pro His Arg Ser Ile Lys Glu Glu Leu Gly His Thr Asn
            100                 105                 110

Gln Gly Asp Arg Thr Arg Ala Leu His Val His Ser Thr Leu Leu Phe
        115                 120                 125

Ala Pro Gln Ser Gln Thr Ile Val Gly Leu Ile Glu Gln Gln Arg Trp
    130                 135                 140

Ser Arg Asp Ile Thr Lys Arg Gly Gln Lys His Gln His Ala Thr Arg
145             150                 155                 160

Pro Tyr Lys Glu Lys Glu Ser Tyr Lys Trp Glu Gln Ala Ser Arg Arg
                165                 170                 175

Val Val Glu Arg Leu Gly Asp Lys Met Leu Asp Val Ile Ser Val Cys
            180                 185                 190

Asp Arg Glu Ala Asp Leu Phe Glu Tyr Leu Thr Tyr Lys Arg Gln His
        195                 200                 205

Gln Gln Arg Phe Val Val Arg Ser Met Gln Ser Arg Cys Leu Glu Glu
    210                 215                 220

His Ala Gln Lys Leu Tyr Asp Tyr Ala Gln Leu Pro Ser Val Glu
225             230                 235                 240

Thr Lys Ala Leu Thr Ile Pro Gln Lys Gly Gly Arg Lys Ala Arg Asn
                245                 250                 255

Val Lys Leu Asp Val Lys Tyr Gly Gln Val Thr Leu Lys Ala Pro Ala
```

```
              260                 265                 270
Asn Lys Lys Glu His Ala Gly Ile Pro Val Tyr Tyr Val Gly Cys Leu
            275                 280                 285

Glu Gln Gly Thr Ser Lys Asp Lys Leu Ala Trp His Leu Leu Thr Ser
        290                 295                 300

Glu Pro Ile Asn Asn Val Asp Asp Ala Met Arg Ile Ile Gly Tyr Tyr
305                 310                 315                 320

Glu Arg Arg Trp Leu Ile Glu Asp Phe His Lys Val Trp Lys Ser Glu
                325                 330                 335

Gly Thr Asp Val Glu Ser Leu Arg Leu Gln Ser Lys Asp Asn Leu Glu
            340                 345                 350

Arg Leu Ser Val Ile Tyr Ala Phe Val Ala Thr Arg Leu Leu Ala Leu
        355                 360                 365

Arg Phe Met Asn Glu Ser Asp Glu Leu Ser Lys Ser Cys Glu Pro
    370                 375                 380

Ile Leu Lys Gly Lys Ala Trp Lys Leu Met Trp Leu Lys Leu Glu Arg
385                 390                 395                 400

Lys Gly Leu Pro Lys Glu Ala Pro Asp Ile Ser Trp Ala Tyr Lys Gly
                405                 410                 415

Ile Ala Arg Leu Gly Gly Trp Lys Asn Thr Lys Arg Thr Gly Arg Ala
            420                 425                 430

Ser Ile Lys Thr Leu Trp Gln Gly Trp Phe Arg Leu Gln Thr Ile Leu
        435                 440                 445

Glu Gly Tyr Glu Leu Ala Lys Ser Leu Asp Ser Pro Asp Leu
    450                 455                 460

<210> SEQ ID NO 14
<211> LENGTH: 462
<212> TYPE: PRT
<213> ORGANISM: Artificial Sequence
<220> FEATURE:
<223> OTHER INFORMATION: Full length sequence of chimeric transposon of
      Vibhar and Vibrionales bacterium SWAT-3

<400> SEQUENCE: 14

Met Thr His Ser Asp Ala Lys Leu Trp Ala Gln Glu Gln Phe Gly Gln
1               5                   10                  15

Ala Gln Leu Lys Asp Pro Arg Arg Thr Gln Arg Leu Ile Ser Leu Ala
            20                  25                  30

Thr Ser Ile Ala Asn Gln Pro Gly Val Ser Val Ala Lys Leu Pro Phe
        35                  40                  45

Ser Pro Ala Asp Met Glu Gly Ala Tyr Arg Phe Ile Arg Asn Glu Asn
    50                  55                  60

Ile Asn Ala Glu Asp Ile Ala Glu Ala Gly Phe Gln Ser Thr Val Ser
65                  70                  75                  80

Arg Ala Asn Glu His Lys Glu Leu Leu Ala Leu Glu Asp Thr Thr
                85                  90                  95

Leu Ser Phe Pro His Arg Ser Ile Lys Glu Leu Gly His Thr Asn
            100                 105                 110

Gln Gly Asp Arg Thr Arg Ala Leu His Val His Ser Thr Leu Leu Phe
        115                 120                 125

Ala Pro Gln Ser Gln Thr Ile Val Gly Leu Ile Glu Gln Gln Arg Trp
    130                 135                 140

Ser Arg Asp Ile Thr Lys Arg Gly Gln Lys His Gln His Ala Thr Arg
145                 150                 155                 160
```

```
Pro Tyr Lys Glu Lys Glu Ser Tyr Lys Trp Glu Gln Ala Ser Arg
            165                 170                 175
Val Val Glu Arg Leu Gly Asp Lys Met Leu Asp Val Ile Ser Val Cys
        180                 185                 190
Asp Arg Glu Ala Asp Leu Phe Glu Tyr Leu Thr Tyr Lys Arg Gln His
            195                 200                 205
Gln Gln Arg Phe Val Val Arg Ser Met Gln Ser Arg Cys Leu Glu Glu
        210                 215                 220
His Ala Gln Lys Leu Tyr Asp Tyr Ala Gln Ala Leu Pro Ser Val Glu
225                 230                 235                 240
Thr Lys Ala Leu Thr Ile Pro Gln Lys Gly Gly Arg Lys Ala Arg Asn
            245                 250                 255
Val Lys Leu Asp Val Lys Tyr Gly Gln Val Thr Leu Lys Ala Pro Ala
        260                 265                 270
Asn Lys Lys Glu His Ala Gly Ile Pro Val Tyr Tyr Val Gly Cys Leu
    275                 280                 285
Glu Gln Gly Thr Ser Lys Asp Lys Leu Ala Trp His Leu Leu Thr Ser
        290                 295                 300
Glu Pro Ile Asn Asn Val Asp Asp Ala Met Arg Ile Ile Gly Tyr Tyr
305                 310                 315                 320
Glu Arg Arg Trp Leu Ile Glu Asp Phe His Lys Val Trp Lys Ser Glu
            325                 330                 335
Gly Thr Asp Val Glu Ser Leu Arg Leu Gln Ser Lys Asp Asn Leu Glu
        340                 345                 350
Arg Leu Ser Val Ile Tyr Ala Phe Val Ala Thr Arg Leu Leu Ala Leu
    355                 360                 365
Arg Phe Met Asn Lys Ser Glu Glu Leu Ser Lys Val Asn Cys Glu Arg
    370                 375                 380
Val Phe Lys Gly Lys Ala Trp Lys Leu Met Trp Leu Lys Leu Glu Lys
385                 390                 395                 400
Lys Glu Leu Pro Asn Glu Ala Pro Asn Ile Ser Trp Ala Tyr Lys Gly
            405                 410                 415
Ile Ala Arg Leu Gly Gly Trp Lys Asp Ser Lys Arg Thr Gly Arg Ala
        420                 425                 430
Ser Ile Lys Val Leu Trp Gln Gly Trp Phe Arg Leu Gln Thr Ile Leu
    435                 440                 445
Glu Gly Tyr Glu Leu Ala Lys Ser Leu Asp Gln Leu Asp Leu
    450                 455                 460

<210> SEQ ID NO 15
<211> LENGTH: 49
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 15
aatgatacgg cgaccaccga gatctacacg ctgacgtcga gacttgtga           49

<210> SEQ ID NO 16
<211> LENGTH: 43
<212> TYPE: DNA
<213> ORGANISM: Artificial Sequence
<220> FEATURE:
<223> OTHER INFORMATION: Oligonucleotide for DNA fragmentation and/or
      amplification and/or sequencing
```

```
<400> SEQUENCE: 16
tttttttttt tgctgacgt cgagacttgt gatcaagaga cag                43

<210> SEQ ID NO 17
<211> LENGTH: 19
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 17
ctgtctcttg atcacaagt                                          19

<210> SEQ ID NO 18
<211> LENGTH: 48
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 18
caagcagaag acggcatacg agatcggtgg agctgtgcgt agatgtga          48

<210> SEQ ID NO 19
<211> LENGTH: 31
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 19
ggagctgtgc gtagatgtga tcaagagaca g                            31

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide for DNA fragmenting and/or
      amplification and/or sequencing

<400> SEQUENCE: 20
tctacactag ttctctgtc                                          19

<210> SEQ ID NO 21
<211> LENGTH: 54
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 21
caagcagaag acggcatacg agatcgtgat cggtggagct gtgcgtagat gtga   54

<210> SEQ ID NO 22
<211> LENGTH: 54
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 22
```

-continued caagcagaag acggcatacg agatacatcg cggtggagct gtgcgtagat gtga    54

<210> SEQ ID NO 23
<211> LENGTH: 54
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 23
caagcagaag acggcatacg agatgcctaa cggtggagct gtgcgtagat gtga    54

<210> SEQ ID NO 24
<211> LENGTH: 54
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 24
caagcagaag acggcatacg agattggtca cggtggagct gtgcgtagat gtga    54

<210> SEQ ID NO 25
<211> LENGTH: 54
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 25
caagcagaag acggcatacg agatcactgt cggtggagct gtgcgtagat gtga    54

<210> SEQ ID NO 26
<211> LENGTH: 54
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 26
caagcagaag acggcatacg agatattggc cggtggagct gtgcgtagat gtga    54

<210> SEQ ID NO 27
<211> LENGTH: 54
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 27
caagcagaag acggcatacg agatgatctg cggtggagct gtgcgtagat gtga    54

<210> SEQ ID NO 28
<211> LENGTH: 54
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 28
caagcagaag acggcatacg agattcaagt cggtggagct gtgcgtagat gtga 54

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 29
gctgacgtcg agacttgtga 20

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 30
ggagctgtgc gtagatgtga 20

<210> SEQ ID NO 31
<211> LENGTH: 41
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 31
agatctacac gctgacgtcg agacttgtga tcaagagaca g 41

<210> SEQ ID NO 32
<211> LENGTH: 35
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 32
cggtggagct gtgcgtagat gtgatcaaga gacag 35

<210> SEQ ID NO 33
<211> LENGTH: 35
<212> TYPE: DNA
<213> ORGANISM: Artificial Sequence
<220> FEATURE:
<223> OTHER INFORMATION: Oligonucleotide for DNA fragmentation and/or
      amplification and/or sequencing

<400> SEQUENCE: 33
ctgtctcttg atcacatcta cgcacagctc caccg 35

<210> SEQ ID NO 34
<211> LENGTH: 18
<212> TYPE: PRT
<213> ORGANISM: Vibrio harveyi

<400> SEQUENCE: 34

Tyr Glu Arg Arg Trp Leu Ile Glu Asp Phe His Lys Val Trp Lys Ser
1               5                   10                  15

Glu Gly

<210> SEQ ID NO 35
<211> LENGTH: 5
<212> TYPE: PRT
<213> ORGANISM: Vibrio harveyi

<400> SEQUENCE: 35

Asp Arg Glu Ala Asp
1               5

<210> SEQ ID NO 36
<211> LENGTH: 19
<212> TYPE: DNA
<213> ORGANISM: Artificial Sequence
<220> FEATURE:
<223> OTHER INFORMATION: Artificial IRL for Vibhar

<400> SEQUENCE: 36
ctgtctcttg atcacaagt                                              19

<210> SEQ ID NO 37
<211> LENGTH: 19
<212> TYPE: DNA
<213> ORGANISM: Artificial Sequence
<220> FEATURE:
<223> OTHER INFORMATION: Artificial IRL sequence for Vibhar

<400> SEQUENCE: 37
acttgtgatc aagagacag                                              19

<210> SEQ ID NO 38
<211> LENGTH: 19
<212> TYPE: DNA
<213> ORGANISM: Artificial Sequence
<220> FEATURE:
<223> OTHER INFORMATION: Artificial IRL for Vibhar

<400> SEQUENCE: 38
ctgtctcttg atcacatct                                              19

<210> SEQ ID NO 39
<211> LENGTH: 19
<212> TYPE: DNA
<213> ORGANISM: Artificial Sequence
<220> FEATURE:
<223> OTHER INFORMATION: Artificial IRL for Vibhar

<400> SEQUENCE: 39
agatgtgatc aagagacag                                              19

<210> SEQ ID NO 40
<211> LENGTH: 19
<212> TYPE: DNA
<213> ORGANISM: Artificial Sequence
<220> FEATURE:
<223> OTHER INFORMATION: Artificial IRR for Vibhar

<400> SEQUENCE: 40
acttgtgatc aagagacag                                              19

<210> SEQ ID NO 41
<211> LENGTH: 19
<212> TYPE: DNA
<213> ORGANISM: Artificial Sequence
<220> FEATURE:
<223> OTHER INFORMATION: Artificial IRR for Vibhar

```
<400> SEQUENCE: 41
ctgtctcttg atcacaagt                                              19

<210> SEQ ID NO 42
<211> LENGTH: 12
<212> TYPE: PRT
<213> ORGANISM: Artificial Sequence
<220> FEATURE:
<223> OTHER INFORMATION: Linker

<400> SEQUENCE: 42

Thr Thr Thr Thr Thr Thr Thr Thr Thr Thr Thr Thr
1               5                   10
```

IMMOBILIZED TRANSPOSASE COMPLEXES FOR DNA FRAGMENTATION AND TAGGING

CROSS-REFERENCE TO RELATED APPLICATIONS

This application relies on and claims the benefit of the filing date of U.S. provisional patent application No. 61/708,332, filed 1 Oct. 2012, the entire disclosure of which is hereby incorporated herein by reference.

BACKGROUND OF THE INVENTION

Field of the Invention

The present invention relates to the field of molecular biology. More specifically, the invention relates to compositions having a transposase complexed with an oligonucleotide adapter in crude cell lysates or bound to a solid support by way of a specific binding pair linkage, to use of the transposase/oligonucleotide complex in purifying the complex, and to use of the complex to prepare DNA molecules for in vitro amplification, sequencing of nucleic acids, and screening of DNA libraries for sequences of interest.

Description of Related Art

Fragmentation of genomic DNA is a crucial step in DNA sample preparation for high-throughput sequencing, also referred to as next generation sequencing or NGS. Originally used sample preparation methods, such as DNA fragmentation using DNAse I, are very unreliable and often result in DNA fragmentation that is either insufficient or too extensive. In either case, the yield of DNA fragments of useful size (about 200-800 base pairs (bp)) is low. DNA shearing using sonicators, for example E220 and E220x instruments from Covaris (Woburn, Mass.), provides an alternative. However, such instruments are very expensive (over $100,000 in 2012 prices) and overall DNA shearing is a laborious and multi-stage process. It involves DNA fragmentation, fragments ends repair, first fragments purification, poly-A tailing, adapter ligation, second fragments purification, PCR amplification, and third fragments purification. A number of steps can be cut in half using oligonucleotide-transposase complexes, such as the NEXTERA™ DNA sample prep kit from Illumina (San Diego, Calif.). The oligonucleotide-transposase complex provided with the kit can effect both controlled DNA fragmentation and attachment of adapters in a single reaction, which takes only a few minutes. Such complexes are comprised of a dimer of modified Tn5 transposase and a pair of Tn5-binding double-stranded DNA (dsDNA) oligonucleotides containing a 19 bp transposase-binding sequence, or inverted repeat sequence (IR). In the NEXTERA™ system, an engineered, non-native 19 bp transposase binding sequence is used, which provides more efficient DNA fragmentation than the native Tn5 IR sequence. This binding sequence is referred to as "mosaic".

Unlike DNAase, a single molecule of which can generate numerous breaks in a target DNA, the transposase complex is believed to create only one DNA cleavage per complex. Therefore, unlike with DNAse I, the degree of DNA fragmentation is easily controlled during transposase fragmentation by controlling the ratio of transposase complex to target DNA in the reaction mixture. Furthermore, specific nucleotide tags combined with the mosaic sequence can be attached in this transposase-mediated DNA fragmentation process, which is useful for DNA amplification in PCR and attaching the DNA fragments to sequencing chips. Despite obvious advantages in cost, time and labor, the transposase method is less frequently used as compared to sonication because it results in not entirely random fragmentation (bias) of target DNA.

To date the only transposase that is known to be suitable for DNA fragmentation and tagging in NGS is a modified Tn5 transposase. From the onset, Tn5 transposase has been problematic in several respects. First of all, the native transposase was practically impossible to produce, as it is toxic for *E. coli* when expressed from a strong promoter. However, this difficulty was overcome by deleting several N-terminal amino acids (Weinreich et al., J. Bacterial, 176: 5494-5504, 1994). Though this solved the toxicity problem, and the N-terminally truncated transposase was produced at high yield, it possessed very low activity. Therefore, several other mutations were introduced to increase its activity (U.S. Pat. No. 5,965,443; U.S. Pat. No. 6,406,896 B1; U.S. Pat. No. 7,608,434). However, this did not solve all of the problems with the enzyme. For example, the mutated enzyme is stable only in high salt, such as 0.7M NaCl, (Steiniger et al., Nucl. Acids Res., 34: 2820-2832, 2006); it quickly loses its activity at the lower salt conditions that are required for the transposase reaction, with a half-life only 2.4 minutes in the reaction mixture. Thus, DNA fragmentation reactions using this transposase are typically performed in five minutes and very large amounts of enzyme are used. Despite the fact that high salt concentration is maintained throughout the purification process, the purified enzyme is largely inactive; thus, 9.4 times excess of enzyme over oligonucleotides is typically used to form Tn5 transposase-oligonucleotide complexes (Naumann and Reznikoff, J. Biol. Chem., 277:17623-17629, 2002). In addition, the transposase is prone to proteolytic degradation. To address this problem, the degradation-prone sites were mutated. Interestingly, these mutations resulted in drastic reduction of the in vivo activity of the enzyme, but had little effect on the in vitro activity (Twining et al., J. Biol. Chem., 276: 23135-23143, 2001). Overall, Tn5 transposase is difficult to produce, it is required in large amounts, and it is very expensive.

However, as yet, no one has provided an alternative technology. It is generally believed that native unmutated transposases are inherently inactive because high activity would be incompatible with the host cell survival in the environment (Reznikoff W S. Mol. Microbiol., 2003, 47, 1199-206). Because native transposases are believed to possess low activity, they would be unsuitable for NGS sample preparation. In view of the fact that it took many years of mutagenesis and biological selection to render purified Tn5 transposase active, the task of providing another transposase that has suitable activity seems problematic. For example, in an attempt to construct superactive SB transposase for modification of eukaryotic cells, almost every single amino acid in it was mutated, small blocks of amino acids from related transposases were imported, and systematic alanine scanning and rational replacement of selected amino acid residues were applied (Ivies and Izvak, Mobile DNA, 1:25, 1-15, 2010). However, this effort resulted in variants with only modest increases in activity. Only a high throughput approach for combining such variants resulted in a variant with desired activity. An additional difficulty in obtaining a suitable transposase is that, even assuming that a native transposase is sufficiently active for in vitro manipulations, transposase activity might be lost during its purification process when it is subjected to the unnatural environments that are typically employed during conventional protein purification, i.e., high or low salt, alkaline or acidic pH, detergents, attachment to resins, absence of putative co-factors, etc.

As discussed below, the inventor addressed and solved the problems in the art by devising a new process for obtaining purified, active transposases. The solution obviated the need for conventional transposase purification by first forming the complex of transposase with oligonucleotides in crude cell lysates, which is a more physiological environment than employed in prior schemes, and more sparing for transposase activity, and then purifying the complex. An advantage of this approach is that transposase complexes with oligonucleotides are formed prior to the transposase purification. Another advantage of this approach is that it avoids the expensive and time consuming process of transposase purification seen in other technologies. Furthermore, attaching a transposase complex to a solid support, such as plates or beads, provides a technical solution for high throughput plate or bead format sample preparation for NGS.

SUMMARY OF THE INVENTION

The present inventor has recognized that there is a need in the art for improved transposase-mediated DNA fragmentation systems. Among the needs in such systems are transposases and transposases complexed with other substances, which have superior properties and characteristics for DNA fragmentation, including not only improved activity, but improved stability and a more random fragmentation of target DNA as well, as compared to current commercially available Tn5-derived transposases. The systems can include compositions comprising transposases and transposase complexes having superior properties and characteristics as compared to current commercially available Tn5-derived transposases. In addition, the inventor has recognized that new methods for making or making and purifying transposases and transposases complexed with other substances are needed to provide transposases with higher activity and better stability than the Tn5-derived transposases now commercially available. Yet further, the inventor has recognized that such improved systems can include use of the improved transposases and transposase complexes to fragment DNA in a more controlled manner, and to produce DNA molecules for use in a variety of other molecular biology processes, including but not limited to, acellular DNA amplification (e.g., PCR) and high-throughput sequencing.

In a first aspect, the present invention provides recombinant wild-type and modified transposases, which in embodiments are isolated or purified. The transposases are considered isolated or purified when they are found in an environment that is different than the environment in which they exist in nature or in which they were produced. For example, they can be in an environment in which some or all of the other biomolecules of the cell in which they are produced are removed. The transposases are recombinant if they are produced in a cell that is not the cell in which they are naturally found, and are modified if they have amino acid sequences that differ from the naturally-occurring sequence(s) of the transposase(s) from which they derive or originate. For example, a transposase according to the invention can have the amino acid sequence of a naturally-occurring transposase (wild-type), or of a modified transposase that has one or more naturally-occurring amino acids deleted or replaced with a different amino acid, or a modified transposase can have amino-acid sequences added to the wild-type sequence. In addition, the naturally-occurring amino acid sequence can be disrupted by addition of one or more amino acids at one or more sites in the sequence. In some embodiments, the transposases are chimeric proteins, i.e., they are proteins that include a mixture of amino acid sequences from two or more different transposases.

The transposases of the invention can be present in compositions, which comprise at least one other substance in addition to the transposase. In certain embodiments, the compositions comprise two or more different transposases. The nature and number of other substances is not particularly limited. In many embodiments, the compositions comprise at least water, although certain embodiments are directed to frozen compositions or dried (e.g., freeze-dried) compositions. In exemplary embodiments, the compositions comprise a transposase in cell lysates or in DNA fragmentation reaction mixtures, which, in embodiments are supplemented with EDTA and/or oligonucleotides. EDTA chelates divalent cations, thus inhibiting host cell nucleases, which typically require $Mg^{2+}$ ions for their activity and otherwise would degrade the oligonucleotides. The fact that formation of the transposase-oligonucleotide complex does not require divalent cations allows for the addition of EDTA or other nuclease inhibitors to crude cell lysates without disruption of the formation of, or maintenance of, the complex.

In another general aspect of the invention, the transposases can be found as part of complexes. Transposase complexes according to the invention comprise at least one transposase of the invention chemically bound through non-covalent bonds, to at least one oligonucleotide. Each oligonucleotide in a complex comprises at least a portion that is double stranded, and can comprise a portion that is single stranded. These oligonucleotides are referred to at times in this document as "adapters". At least one of the oligonucleotides of each complex comprises a specific binding pair member of a specific binding pair, which enables the complex to be attached to a solid substrate (also referred to in the art and herein as a solid support). In exemplary embodiments, the specific binding pair members are streptavidin and biotin.

The complexes may comprise one or more transposase molecules and one or more adapters. In complexes that comprise at least two transposases, at least two of the transposases are bound to an oligonucleotide. In embodiments where the complex comprises two transposases, the complex can represent a form similar to a synaptic complex. Higher order complexes are also possible, for example complexes comprising four transposases, eight transposases, or a mixture of different numbers of sizes of complexes. As alluded to above, in complexes comprising more than two transposases, not all transposases need be bound by an oligonucleotide. Rather, it is sufficient that two of the transposases are bound, although additional oligonucleotides may be bound. Usually, where two or more transposase molecules are present in a complex, the same transposase is employed in the complex. However, in some embodiments, it is preferred that two or more different transposases are employed in a single complex. For example, one or more of the transposase molecules in the complex could be rendered partially or wholly inactive via modification of their amino acid sequences, and a mixture of active and partially or wholly inactive transposase molecules could be used to modulate the distance between active subunits, and consequently the average size of DNA fragments produced by the complex. Likewise, different complexes having different recognition sequences can be used, such as, for example a complex comprising a transposase with a recognition sequence for high GC sequences and another transposase with a recognition sequence for a sequence having lower GC content. Mixing of transposases having different GC and AT content in recognition sequences allows for tailoring of fragmentation patterns for target DNA sequences. Although one type of oligonucleotide adapter can be used to fragment DNA, in embodiments where fragmentation is followed by amplification and sequencing of the fragmented DNA, use of at least two kinds of oligonucleotide adapters is preferred to facilitate PCR amplification of the DNA fragments and to provide different landing sites for different DNA sequencing primers that are used to sequence the DNA fragments in both directions. One or more transposase recognition sequences can be used to design oligonucleotides, as unlike some restriction endonucleases, for instance NindIII, transposases are not necessarily limited to one exact recognition sequence.

As with the transposases of the invention, the transposase complexes of the invention can be present in compositions, which comprise at least one other substance in addition to the transposase complex. The nature and number of other substances is not particularly limited. In many embodiments, the compositions comprise at least water, although certain embodiments are directed to frozen or dried (e.g., freeze-dried) compositions. In exemplary embodiments, the compositions comprise a transposase complex in cell lysates or in DNA fragmentation reaction mixtures.

Another general aspect of the invention is a transposase complex attached to a solid support by way of a linkage. The linkage may be any linkage known in the art for attaching a biochemical molecule to a solid support. In some embodiments, the linkage is severable. Those of skill in the art are aware of numerous such linkages and corresponding removal reagents and techniques. In exemplary embodiments of this aspect, a transposase complex comprising at least two transposases, each bound by an oligonucleotide adapter, where one of the adapters contains a member of a specific binding pair at its end, is chemically bound to a solid substrate by way of binding of the specific binding pair member to its binding partner, which is chemically bound to the solid substrate. While any specific binding pair can be used, in exemplary embodiments, streptavidin and biotin are used. The transposase complex bound to a solid substrate allows not only for purified bound complex, but also for compositions comprising the bound transposase complex, such as cell lysates in which the transposase complex is solid substrate-bound and transposase reaction mixtures, such as DNA fragmentation mixtures.

In another general aspect, the invention provides methods of making transposase complexes. In general, the method comprises adding to a cell lysate comprising one or more transposases one or more adapter oligonucleotides, and allowing the adapters to bind to the transposases to form complexes. Where desired, the method further comprises allowing the transposase complexes to associate with each other to form dimeric and/or higher order complexes. In preferred embodiments, the method also includes inhibiting deoxyribonucleases present in the lysate, for example with calcium ions, chemical compounds (e.g., chelating agents), reducing reagents, 2-nitro-5-thiocyanobenzoic acid, alfa-toxin B2a, G2, G2a, and M1, carbodiimide, cholesterol sulfate, iodoacetate, or proteins, e.g., calf spleen inhibitor protein or actin. In embodiments, the method also comprises producing the transposase in a cell, lysing the cell, or both.

Further, the present invention provides a method of purifying a transposase or a transposase complex. In general, the method comprises lysing a cell containing the transposase, adding an adapter oligonucleotide, which comprises a member of a specific binding pair, to the cell lysate, allowing the adapter to bind to the transposase, contacting the lysate with a solid substrate that comprises the partner for the specific binding pair member, subjecting the lysate and solid substrate to conditions under which the specific binding pair members will bind to each other, and removing some or all of the cell lysate from the solid substrate. In preferred embodiments, the method also includes inhibiting deoxyribonucleases present in the lysate, for example with DNase inhibitors (e.g., chelating agents). The method can further include washing the solid-substrate bound transposase to further purify it from cell lysate material. In embodiments, the method further comprises formation of transposase complexes prior to contacting the cell lysate with the solid substrate. Yet the method also comprises embodiments where the solid substrate is added prior to the formation of transposase complexes or simultaneously with the formation of the complexes. Yet again, in some embodiments, the method comprises dissociating the transposase complexes after purification and/or dissociating the transposase from the adapter after purification.

The purified transposase complexes have numerous uses, as can be envisioned by the ordinary artisan. Among those uses, the present document exemplifies use of the transposase complexes for preparation of DNA to be used in further analytical procedures. One such exemplary use is in fragmenting of DNA to prepare it for acellular amplification (e.g., PCR) or high-throughput sequencing. As such, in one aspect, a method of fragmenting DNA and preferably tagging it with adapters is provided. In general, the method comprises combining target DNA to be fragmented with a transposase complex bound to a solid substrate, and incubating the combination under conditions that are suitable for DNA cleavage by the transposase complex to yield fragmented target DNA bound to the solid substrate. The solid substrate-bound DNA fragments can then be used in any number of analytical reactions. In some embodiments, the components of the reaction mixture that are not bound to the solid substrate are removed, such as by any suitable washing procedure known in the art. In some embodiments, the solid substrate-bound DNA fragments are created and immediately used, without additional purification or preparation. For example, a one-mix DNA fragmentation and amplification mixture can be provided, in which the target DNA is combined with the solid substrate-bound transposase complex under conditions that permit DNA fragmentation to produce solid substrate bound DNA fragments, then the mixture is subjected to conditions that permit acellular amplification of the bound DNA fragments, for example by PCR.

BRIEF DESCRIPTION OF THE DRAWINGS

The accompanying drawings, which are incorporated in and constitute a part of this specification, illustrate embodiments and features of the invention, provide data supporting the written description, and together with the written description, serve to explain certain principles of the invention.

FIG. 1, Panels A-D, depicts a series of steps that can be performed to create a transposase complex, bind the complex to a solid substrate, and use the solid substrate-bound complex to fragment DNA and produce solid substrate-bound DNA fragments.

FIG. 2 depicts the use of solid substrate-bound DNA for in vitro amplification.

DETAILED DESCRIPTION OF VARIOUS EMBODIMENTS OF THE INVENTION

Figure 3:
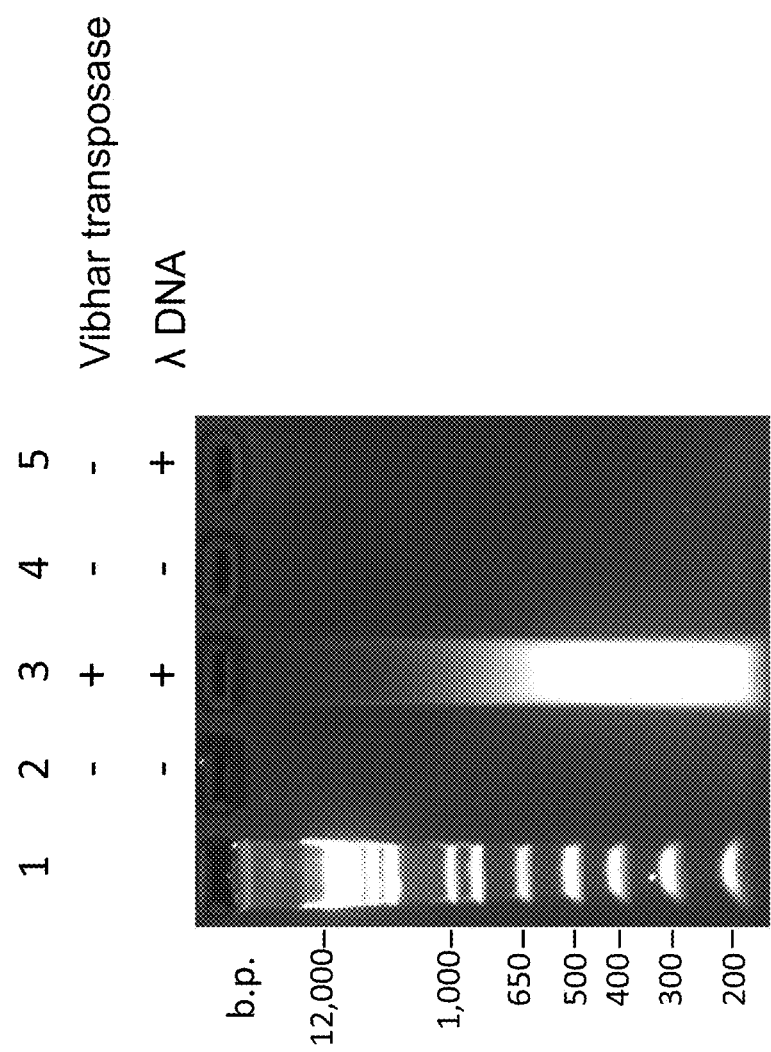
FIG. 3 depicts a picture of an agarose gel stained for DNA, showing that transposase ("Vibhar") complexes with transposase-specific oligonucleotides that were formed in crude cell lysates and bound to a solid substrate, and isolated from the lysates in the bound form (i.e., purified immobilized complexes) can be used to fragment target DNA (phage lambda DNA) and the fragments can be specifically amplified in PCR. Lane contents: lysates of *E. coli* cells that express Vibhar transposase (lane 3) or lysates of negative control cells that do not express Vibhar transposase (lanes 2, 4, 5) applied with target DNA (lanes 3 and 5) or without the target DNA (lanes 2 and 4). For comparison, 1 kb+ DNA ladder (Life Technologies, Carlsbad, Calif.) was run on lane 1.

Reference will now be made in detail to various exemplary embodiments of the invention, data supporting such embodiments being illustrated in the accompanying drawings. This detailed description is not to be considered a limitation of the invention, but should rather be understood as a disclosure that provides the reader a more detailed description of certain aspects, features, and embodiments of the invention.

Before embodiments of the present invention are described in detail, it is to be understood that the terminology used herein is for the purpose of describing particular embodiments only, and is not intended to be limiting. Further, where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. To be clear, where a set of values or a range of values is disclosed, it is to be understood that each value falling within the two values or the range of values is encompassed by the invention, and the omission of a specific recitation of each particular value is made for the convenience of the reader and to reduce the size of this document. The skilled artisan will immediately understand which values are encompassed by ranges disclosed herein without the need for each and every value to be specifically disclosed in this document.

Unless defined otherwise, all technical and scientific terms used herein have the same meaning as commonly understood by one of ordinary skill in the art to which the term belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a transposase" includes a plurality of such transposases and reference to "the sample" includes reference to one or more samples and equivalents thereof known to those skilled in the art, and so forth. Furthermore, the use of terms that can be described using equivalent terms include the use of those equivalent terms.

A first aspect of the invention is a transposase having DNA fragmenting activity in vitro. The transposase of the invention can be any protein having transposase activity in vitro. It can be a naturally occurring transposase or a recombinant transposase. The transposase can be isolated or purified from its natural environment (i.e., cell nucleus or cytosol), at least to some extent. Preferably, the transposase is recombinantly produced, and preferably is isolated or purified from the recombinant host environment (i.e., cell nucleus or cytosol), at least to some extent. Most preferably, the transposase is purified away from other cellular components to a level of 90% or greater prior to inclusion in compositions of the present invention. Preferably, the transposase is at a level of about 95% or greater, such as about 98% pure, about 99% pure, or greater than 99% pure. Purity is determined based on common techniques for determining purity, such as by Coomassie blue staining of protein gels, silver staining of protein gels, HPLC, mass spectrometry, or other sensitive techniques for detecting impurities in protein samples. DNA impurities can also be assessed, e.g., using PCR. In exemplary embodiments, the transposase is a transposase with a "cut and paste" mechanism of transposition (Yuan and Wessler, Proc Natl Acad Sci USA. 2011 May 10; 108(19):7884-9), and is a member of the IS4 family of transposases, such as one that is naturally found in *Vibrio* species, including, but not limited to, *Vibrio harveyi*. In embodiments, the transposase is not the Tn5 transposase or a transposase derived from the Tn5 transposase, for example by mutagenesis of the wild-type Tn5 transposase.

Figure 4:
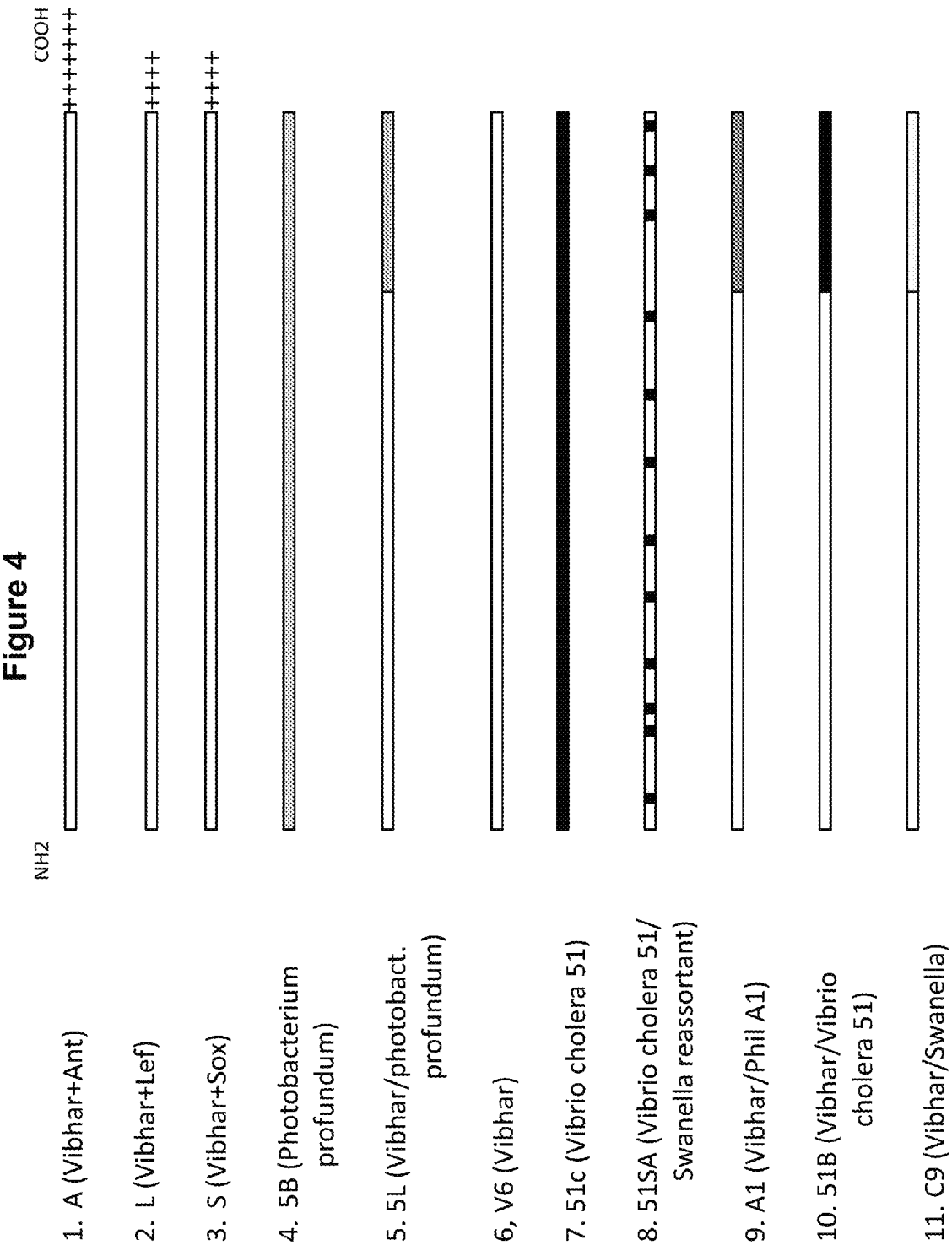
FIG. 4 schematically describes certain exemplary transposases encompassed by the present invention. Where a transposase is a chimera of two or more transposases, the various combined sequences are depicted in different shades of grey, the annotation on the left side indicating the order the sequences. 1. A (Vibhar+Ant), *Vibrio harveyi* transposase (YP_001446289; SEQ ID NO:1) with a C-terminal extension of GGGRQIKIWFQNRRMKWKKEN (SEQ ID NO:2)—the full sequence is provided as SEQ ID NO:3; 2. L (Vibhar+Lef) *Vibrio harveyi* transposase with a C-terminal extension of GGGKKKRKRER (SEQ ID NO:4)—the full sequence is provided as SEQ ID NO:5; 3. S (Vibhar+Sox) *Vibrio harveyi* transposase with C-terminal extension of GGGKYRPRRRKQ (SEQ ID NO:6)—the full sequence is provided as SEQ ID NO:7; 4. 5B-*Photobacterium profundum* SS9 transposase (YP_133439; SEQ ID NO:8); 5. 5L *Vibrio harveyi* transposase with its C-terminal domain substituted for the corresponding C-terminal domain from *Photobacterium profundum* SS9 transposase (full sequence of chimera provided as SEQ ID NO:9); 6. V6, *Vibrio harveyi* transposase (YP_001446289; SEQ ID NO:1); 7. *Vibrio cholerae* V51 transposase (ZP_04918286.1; SEQ ID NO:10); 8. *Vibrio cholerae* V51 transposase (ZP_04918286.1) with amino acids changed to conform to *Vibrionales* bacterium SWAT-3 transposase (ZP_01815141.1; full sequence of chimera provided as SEQ ID NO:11); 9. *Vibrio* harveyi transposase with its C-terminal domain substituted for the corresponding C-terminal domain from IS4 family transposase TnpA [*Legionella pneumophila* subsp. *pneumophila* str. Philadelphia 1] (full chimeric sequence provided as SEQ ID NO:12); 10. *Vibrio harveyi* transposase with its C-terminal domain substituted for the corresponding C-terminal domain from *Vibrio cholerae* V51 transposase (full chimeric sequence provided as SEQ ID NO:13); 11. *Vibrio harveyi* transposase with its C-terminal domain substituted for the corresponding C-terminal domain from *Vibrionales* bacterium SWAT-3 transposase (ZP_01815141.1; full chimeric sequence provided as SEQ ID NO:14).

An exemplary embodiment of the invention relates to the *Vibrio harveyi* transposase, the discovery and characterization of being disclosed in co-pending U.S. patent application Ser. No. 13/470,087, filed 11 May 2012, the entire content of which is hereby incorporated herein by reference. The naturally occurring enzyme sequence is available as hypothetical protein VIBHAR_03113 [*Vibrio harveyi* ATCC BAA-1116] under NCBI/GenBank Accession No. YP_001446289, and is referred to herein at times as "Vibhar" (SEQ ID NO:1). Other exemplary embodiments of transposases according to the invention are those described with reference to FIG. 4, including SEQ ID NOs:3, 5, and 7-14.

While the naturally occurring Vibhar transposase is exemplified herein, it is to be understood that other naturally occurring transposases with cut and paste mechanisms of insertion (e.g., IS50 transposase, also called Tn5 transposase) are included within the scope of this invention. Furthermore, engineered transposases (e.g., transposase having modified Tn5 transposase sequences), which are derived from naturally occurring transposases but include one or more amino acid deletions, substitutions, or additions, are also encompassed. Further, chimeric transposases are encompassed by the invention. It is to be understood that the modifications made to the naturally occurring transposases do not abolish the transposase activity of the enzyme, although the modifications may alter the specificity or activity in some way. Those of skill in the art can recognize residues that are important in function of the various transposases encompassed by the invention with reference to conserved residues among transposases based on alignment of sequences of transposases. Preferably, the engineered transposases share at least 50% sequence identity with a naturally occurring transposase, preferably the transposase from which the engineered enzyme is derived. Other preferred levels of identity include at least 60%, at least 70%, at least 80%, at least 90%, at least 95%, at least 98%, and at least 99%. Again, those of skill in the art will immediate recognize that all specific values for percent identity falling within these ranges are contemplated by the invention, without the need for Applicant to specifically list all of the values herein.

For example, residues D93, D193, and E327 (amino acid numbering based on the amino acid sequence of GenBank Accession No. YP_001446289.1) are active site residues. Those of skill in the art would immediately recognize that those residues should be maintained if the purpose of making a recombinant protein is to retain enzymatic activity, but would target those residues if a non-active enzyme was desired, or if an enzyme with altered activity were desired (e.g., by making conservative changes or changes that conserved the three-dimensional presentation at one or more of these residues). Further, one of skill in the art would recognize that the following residues should be avoided as sites of mutation if little or no change in activity for the recombinant enzyme were desired, but would be targeted if altered activity were desired: W9, L19, D21, R23, R27, L28, A56, Y57, R58, N62, I70, T78, T94, L108, G109, H123, L127, G137, Q141, R146, K165, E166, W170, R194, E195, D197, R206, 8215, L229, 8255, L296, L301, L302, P306, A313, Y320, R323, W324, H330, K334, G337, E341, R353, A362, R364, L386, L394, A413, L420, G422, K427, W438, and G440. Additionally, one of skill in the art would understand the importance of the conserved "YERRWLIEDFHKVWKSEG" (SEQ ID NO:34) motif (residues 320-337 of GenBank Accession No. YP_001446289.1), which is involved in the enzymatic activity of the IS4 family of transposases; the importance of the conserved "DDT" motif (residues 88-99 of GenBank Accession No. YP_001446289.1), which is involved in catalysis and contact of the transposase with target DNA phosphate backbone in the IS4 family of transposases; and the importance of the conserved "DREAD" (SEQ ID NO:35) motif (residues 193-197 of GenBank Accession No. YP_001446289.1), which is involved in target and/or donor DNA binding. Yet again, those of skill in the art would understand the importance of residue W299, which is involved in the hairpin cleavage mechanism of the enzyme. Other residues of interest for structure-function considerations in making recombinant transposases are the various residues described in the literature (e.g., Reznikoff, et al., Journal of Bacteriology, Vol. 186, No. 24, p. 8240-8247, 2004; Yuan and Wessler, Proc Natl Acad Sci USA., Vol. 108, No. 19, p. 7884-7889, 2011, incorporated herein by reference in their entireties). Yet other residues that can be targeted (or avoided) will be apparent from a sequence alignment of the Tn5 protein (YP_788129) and the Vibhar protein (YP_001446289).

While not being limited to any particular transposases, various exemplary transposases according to the invention are disclosed herein, as discussed in more detail below. Based on the recognized structure-function relationships of various amino acid residues and motifs discussed above and the experimental data relating to wild-type and chimeric transposases discussed below, it will be evident to the skilled artisan that, although there might be some variation among the activities of transposases, the invention is not limited by the type of transposase selected.

Another aspect of the invention relates to compositions comprising the transposases of the invention. The compositions of this aspect of the invention can be created for any number of purposes, and are not limited to those specifically discussed herein. Exemplary compositions are those useful for storing transposases, for cleaving or fragmenting target DNA, and for cleaving and tagging target DNA. In addition, exemplary compositions comprise the transposase of the invention in a cell lysate. In general, compositions comprising the transposases of the invention are compositions for production of the transposases, compositions for purification of the transposases, compositions for storage of the transposases, and compositions for use of the transposases. As such, any of the various known transposase reaction compositions are encompassed by the present invention, as are aqueous storage compositions. The skilled artisan is aware of such compositions, and it is well within the skill level to adjust the conditions (e.g., by altering the concentrations of certain ions or altering the pH) to alter one or more characteristics of the compositions to suit a particular need. For instance, transposase reaction conditions are described in Vaezeslami et al., Bacteriol., 189(20): 7436-7441, 2007. Typically, the reaction includes a stage of loading the transposase with adapters at a pH range of 6-9, preferably pH 7-8, in a 20-200 mM buffer, for example Tris buffer, which includes salt, such as KCl, at about 0.1-0.8 M, and 5-50% glycerol. The adapters are provided at 5-300 mM. Typically, transposase is provided at 0.2-20 mg/ml. At the next stage, transposase complexes are mixed with target DNA in the presence of about 1-100 mM, preferably about 5-20 mM $Mn^{2+}$ or $Mg^{2+}$ ions. Usually, target DNA is present at about 0.000001-200 ug/ml, such as 0.5-200 ug/ml, preferably at about 10-100 ug/ml. As was demonstrated in co-pending U.S. patent application Ser. No. 13/470,087, filed 11 May 2012, $Mn^{2+}$ ions can be used instead of $Mg^{2+}$ ions.

The transposases according to the invention, when used to fragment DNA, are preferably present in complexes comprised of at least two transposases, where at least two of the transposases of each complex are associated, by way of chemical bonding, to DNA oligonucleotides, which are at least partially double stranded. For ease of reference and as mentioned above, such oligonucleotides are referred to herein at times simply as "adapters". In highly preferred embodiments, the complexes comprise two transposases, each bound by an adapter. The highly preferred transposase/adapter complexes are depicted graphically in FIG. 1, for example. Within the transposase complexes, each transposase can be the same, or have the same recognition sequence for DNA. Alternatively, if the transposases can recognize sequences that differ in several nucleotides, the recognition sequences can differ (see, e.g., co-pending U.S. patent application Ser. No. 13/470,087, filed 11 May 2012). Yet again, the two can differ in identity and/or recognition sequences. Where the two transposases have different recognition sequences, the adapters are suitably designed such that each transposase can bind an adapter.

The adapters are chemically bound to the transposases of the complex at double-stranded DNA (dsDNA) regions of the adapters. The dsDNA regions comprise recognition sequences for the transposases. The adapters in a particular complex can, but do not necessarily, comprise a single recognition sequence for a particular transposase. In embodiments, the adapters can comprise two or more recognition sequences for the same transposase. Alternatively, where two different transposases are in a complex, and each has a different recognition sequence, one adapter of the complex will have the recognition sequence for one of the transposases and the other adapter will have the recognition sequence for the other transposase.

In addition to the dsDNA recognition sequence regions, typically the adapters comprise at least one other region, which is designed for primer binding for amplification or other polymerization reactions. The primer binding regions can be double-stranded or single-stranded and can be designed to include any suitable primer binding sequence. It is a routine task for the skilled artisan to design a primer binding sequence and corresponding primer, and it is left to the practitioner to devise suitable sequences for use in primer binding and extension.

The adapters can further comprise one or more dsDNA or single-stranded DNA (ssDNA) sequences (also referred to herein as "tags"). The tags can be included to allow attachment of generated DNA fragments to sequencing chips, such as Illumina chips (as known in the art), and allow identification of the source of the target DNA library, such as Index sequences. For the purpose of applicability to next generation sequencing, it is preferred that about a half of the adapter ends are tagged with one type of tag and another half with a different tag, such that after transposase-mediated fragmentation of a target DNA, one kind of tag is attached to one end of the target DNA fragment, and another type to the opposite end to allow reading of a DNA fragment in both directions. The inventor has recognized that improved DNA fragmentation results for preparation of fragments for further analysis (i.e., improved randomization of fragmentation) can be achieved by combining two different transposase recognition sequences, i.e., that some (e.g., about 50%) of the adapters in a particular composition comprise a first recognition sequence for a transposase and the remaining adapters comprise a second, different recognition sequence. The recognition sequence can be a naturally occurring sequence for the transposase, or can be an engineered sequence that provides additional or alternative functions for the adapter.

In exemplary embodiments, the recognition sequence differs for each end of the target DNA to be fragmented. In some embodiments, the two sequences are identical or substantially identical, having at least 90% (i.e., 90%-100%) sequence identity with each other. In some other embodiments, the two sequences are different, having less than 90% (i.e., 89% or less, a minimum being about 30%) identity with each other. However, it is preferred that both recognition sequences are recognizable by the transposase being used in conjunction with them to about the same degree. To this end, the efficiency of transposase fragmentation can be assessed separately for several recognition sequence and recognition sequences with practically the same efficiency are selected for use together. In exemplary embodiments, the recognition sequences comprise both natural and modified *V. harveyi* sequences i.e., the sequence: 5'-ctgtctcttgatcacaagt-3' (SEQ ID NO:36), which is a natural IRL sequence, and its complement 5'-acttgtgatcaagagacag-3' (SEQ ID NO:37); modified IRL sequence 5'-ctgtctcttgatcacatct-3' (SEQ ID NO:38), and its complement 5'-agatgtgatcaagagacag-3' (SEQ ID NO:39). The natural *V. harveyi* IRR recognition sequence can be used also, 5'-acttgtgatcaagagacag-3' (SEQ ID NO:40) and its complement 5'-ctgtctcttgatcacaagt-3' (SEQ ID NO:41). Furthermore, a single type of natural or modified recognition sequence can be used, or simultaneously two or more types of natural or modified recognition sequences, such as those for *V. harveyi*, in any combination, can be used. One of skill in the art can use any transposase and easily discern its recognition sequence, as recognition sequences are known to be present as IRR and IRL repeats flanking transposase genes.

One skilled in the art will recognize that any nucleotide sequences can easily be attached to the recognition sequences during oligonucleotide synthesis or by other methods, e.g., using DNA ligase. Such sequences can provide landing sites for sequencing primers and for PCR primers in order to amplify DNA fragments and also serve the purpose of attaching the DNA fragments to DNA sequencing chips, such as Illumina chips. Additional nucleotide sequences are preferably single-stranded or mostly single-stranded, otherwise the transposase might be inhibited, as it would recognize excessive dsDNA as a substrate. Though to a much smaller degree, attachment of single-stranded extensions can also reduce transposase activity, therefore it is preferable to keep the size of the attachments to a minimum. To this end, use of two different recognition sequences is preferred. In that way, landing sites for primers can be extended into the part of the recognition sequences that differs between the two (see, e.g., co-pending U.S. patent application Ser. No. 13/470,087, filed 11 May 2012). This design allows for the use of only two primers for PCR amplification of DNA fragments as compared to four primers in the NEXTERA™ system, which uses the same transposase recognition sequence for both adapters. The use of two, rather than four, primers is an advantage of the prior system in that it is simpler and more efficient.

Figure 5:
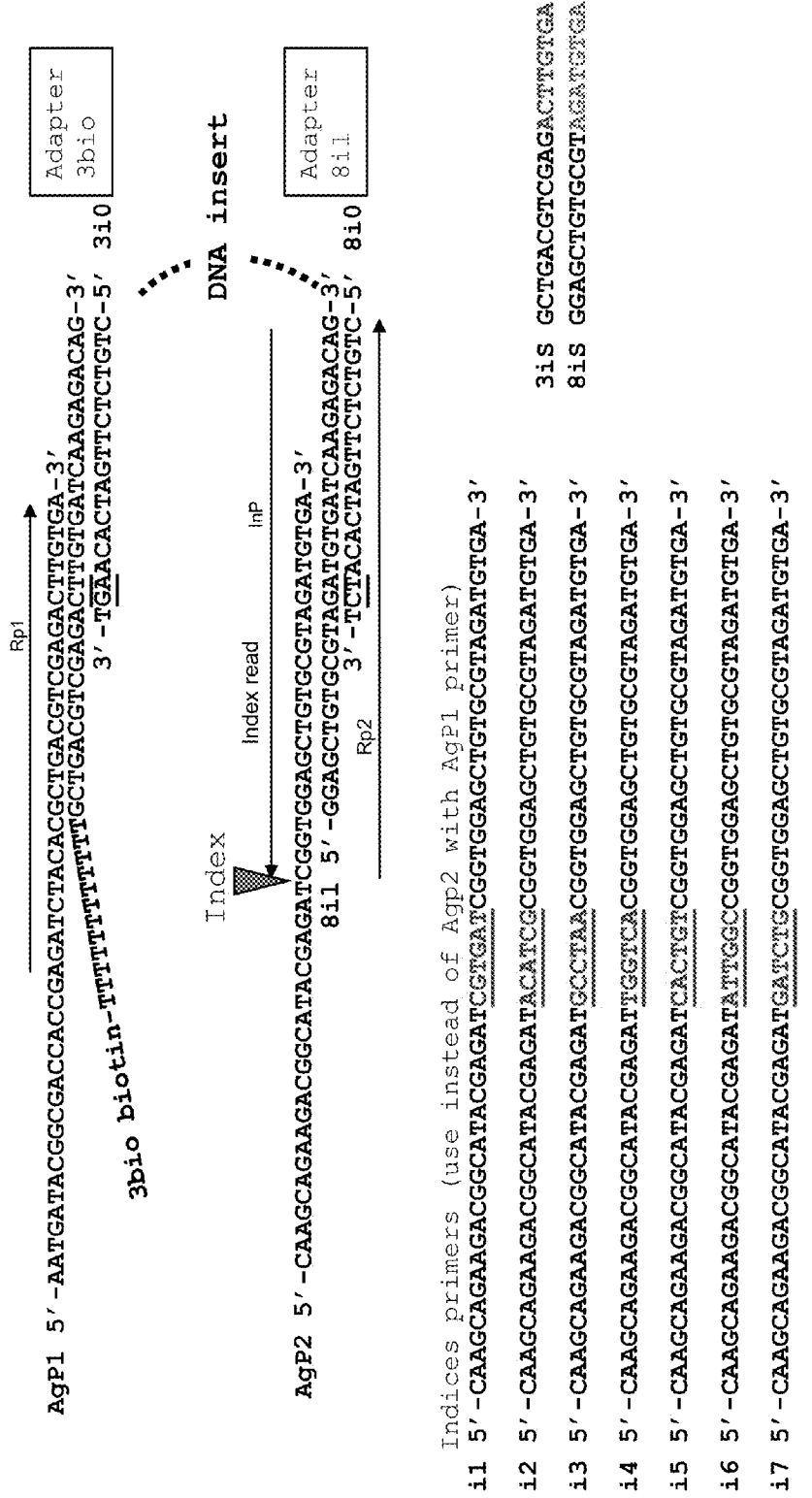
FIG. 5 depicts adapters and primers for PCR amplification, and oligonucleotides for sequencing on Illumina instruments. AgP1=SEQ ID NO:15; 3bio=SEQ ID NO:16; 3i0=SEQ ID NO:17; AgP2=SEQ ID NO:18; 8i1=SEQ ID NO:19; 8i0=SEQ ID NO:20; i1=SEQ ID NO:21; i2=SEQ ID NO:22; i3=SEQ ID NO:23; i4=SEQ ID NO:24; i5=SEQ ID NO:25; i6=SEQ ID NO:26; i7=SEQ ID NO:27; i8=SEQ ID NO:28; 3iS=SEQ ID NO:29; 8iS=SEQ ID NO:30; Rp1=SEQ ID NO:31; Rp2=SEQ ID NO:32; InP=SEQ ID NO:33.

A unique feature of the transposase complexes of the invention is the inclusion of a member of a specific binding pair in at least one adapter of a complex. The member is covalently attached to the nucleic acid of the adapter and allows for specific binding of the complex to the other member of the specific binding pair. In exemplary embodiments, the other member of the specific binding pair is attached to a solid substrate. In this way, the transposase complex can be specifically bound to the solid substrate, which facilitates purification of the complex and use of the complex to produce solid-substrate bound transposase cleavage products (e.g., DNA fragments for amplification/ characterization). As shown in FIG. 5, attachment of a binding pair member, e.g., biotin, via the 5' end of one strand of an adapter is preferred. However, binding pair member(s) can also be attached to the 3' end or to both 3' and 5' ends that are distant from the "DNA insert" position shown on FIG. 5. Attachment of binding pair member at the "DNA insert" position is not preferred as it is expected to inhibit activity of transposase complexes. Attachment of the complexes to solid supports can be also achieved via the transposase moiety of the complexes that carries a tag which allows attachment to solid supports. For, instance a biotin tag can be attached to a recombinant transposase via C-terminal or N-terminal streptavidin-binding peptide (Keefe et al., Protein Expr Purif., Vol. 23, No. 3, p. 440-446, 2001; Duffy et al., Anal Biochem., Vol. 262, No. 2, p. 122-128, 1998) and the complex can be attached to streptavidin-coated beads or plates. There are many such tags that can be used by those skilled in the art. Any suitable specific binding pairs can be used in accordance with the invention, wherein at least one member of the pair is immobilized on a solid support, and the skilled artisan is free to choose an appropriate pair based on any number of considerations. A non-exclusive listing of binding pairs includes: avidin or streptavidin and biotin; a nano-tag and streptavidin (see, for example, Lamla and Erdmann, Protein Expr Purif. Vol. 33, No. 1, p. 39-47, 2004), an antibody (or antigen-binding portion thereof) and the antigen/epitope to which it specifically binds, e.g., Myc of FLAG tag; an enzyme-substrate pair, e.g., glutathione transferase and reduced glutathione; poly-histidine and a nickel-based resin; aptamers and their specific target molecules, and Si-tag and silica particles (see, for example, Motomura et al., Protein Expr Purif., Vol 77, No. 2, p. 173-177, 2011).

The invention further encompasses compositions comprising transposase complexes. The compositions are not particularly limited in the number and type of substances present. In general, liquid compositions comprise water and the transposase complexes. Typically, one or more other substance is present, such as a salt, an ion, a buffering compound, a metal, or one or more biomolecules. In general, any number of substances can be included in the compositions of this aspect of the invention. The identity, number, and amount of the various additional components will typically be dictated by the application for the composition or the specific requirements for a particular transposase complex for optimal activity.

In exemplary embodiments, a composition of this aspect of the invention comprises one or more transposase complexes in cell lysates of cells in which the transposases are produced (and to which adapters have been added before or after cell lysis). In related exemplary embodiments, the transposase complexes are present in cell lysates, but found in a form that is bound to a solid substrate by way of a specific binding pair linkage. Binding of the complexes to the solid substrate allows for facile purification of the complexes from the other substances present in the cell lysates. As such, various compositions according to the invention include solid substrate-bound complexes in various stages of purification from other cell lysate materials. During the process of purification, the solid substrate-bound complexes can be found in compositions that include washing solution components (as known in the art).

Purified transposase complex compositions, whether the complex is free in solution or bound to a solid substrate, can also be included in enzymatic reaction compositions, such as DNA cleavage/fragmenting reactions. Non-limiting exemplary substances that can be present in compositions according to this aspect of the invention include: target DNA to be cleaved by the transposase complexes, oligonucleotide primers for polymerization of target DNA fragments; one or more DNA polymerases; restriction endonucleases; DNA modifying enzymes; polysaccharides; lipid membranes; nanoparticles; beads, including magnetic beads; transfection reagents; and detergents.

As used herein, the terms "solid substrate" and "solid support" are used in accordance with their meaning in the art. They are thus any material known in the art as suitable for binding and retaining nucleic acids under conditions of purification and/or enzymatic reaction. Those of skill in the art are well aware of suitable materials to use as solid substrates without the need for an exhaustive list to be presented herein. Non-limiting examples of solid substrates useful in the present invention include: nylon, yttrium silicate (YSi), and polyvinyltoluene (PVT) beads, including magnetic beads (see, e.g., Dorgan et al., Journal of Magnetism and Magnetic Materials, Vol. 194: p. 69-75, 1999); nylon, nitrocellulose, or PVDF membranes; and plastic surfaces, such as those comprising polystyrene or polypropylene, the latter found on plates or wells for PCR amplification of nucleic acids, e.g., streptavidin-coated STREP Thermo-Fast PCR plates (Abgene, Surrey, UK). Solid supports can be chemically modified, e.g., aminated (primary or secondary amine) or carboxylated to facilitate attachment of a particular binding pair.

One advantage of using solid support-bound transposase complexes derives from the fact that one adapter is bound to the solid support. As such, when the transposase complex cleaves the target DNA, the target DNA becomes captured on the solid support via the adapter. Replacement of the enzyme with the target as a result of the reaction is an elegant way to produce DNA fragments that can easily be purified from reaction components. It is also an elegant way to produce DNA fragments that can be subjected to various reactions without the need for multi-step purification of the DNA fragments, as they can be purified easily by simply washing.

In another general aspect, the invention provides a method of making transposase complexes. In general, the method comprises lysing cells that contain one or more transposases, adding adapter oligonucleotides that contain recognition sequence(s) for the transposase(s), and allowing the adapters to bind to the transposases to form complexes. The steps of "allowing" comprise providing conditions under which the recited actions occur. Such conditions can be any suitable conditions, including, but not limited to incubation of the cell lysates at from about 0° C. to about room temperature (i.e., about 21° C.-25° C.) for several hours (e.g., 5-14 hours). Higher temperatures and shorter incubation times can be used, but are less preferred due to a possibility of loss of transposase activity in the crude lysates. The method can further include producing the transposases, the adapters, or both. Where the method comprises producing the transposases, the method includes expressing the transposase in a host cell prior to lysing the cell. The transposase can be expressed in the cell in which it is naturally found, or can be expressed recombinantly in a host cell that is not its native host cell. Numerous host cells for recombinant production of proteins are known in the art, e.g., bacterial, yeast, plant, insect, or mammalian cells, and the practitioner is free to select any suitable host cell. In exemplary embodiments, *E. coli* cells are used as host cells for recombinant production of transposases.

In embodiments, the method of making a transposase complex includes producing adapters. The adapters are designed to specifically bind to the transposase(s) being produced. As such, the recognition sequence that must be present on each adapter is known before synthesizing the adapters. Natural recognition sequences often constitute inverted repeats that can be found 50-200 nucleotides upstream and immediately downstream of a transposase open reading frame and can be identified in the genome sequences by those skilled in the art. The adapters can be made using any suitable technique, including chemical synthesis. The adapters include at least a portion that is double stranded. As such, prior to use it is preferred that the two complementary portions be exposed to each other under conditions whereby hybridization occurs to produce the double-stranded portions.

As discussed above, to facilitate purification and to allow for production of solid substrate-bound DNA fragments, one adapter for each transposase complex comprises a member of a specific binding pair. The specific binding pair member is covalently linked to the adapter, preferably at its 5' end, as shown in FIG. 5. Linking can be by way of any suitable technique known for chemically linking substances to nucleic acids. The only limitations are that the specific binding pair member should not interfere with binding of the adapter to the transposase, abolish the activity of the transposase when bound to the solid substrate, or impede amplification of a solid substrate-bound DNA fragments in PCR. To this end, linkers can be provided between a specific binding pair member and the recognition sequences, for example the TTTTTTTTTTTT (SEQ ID NO:42) DNA sequence in Adapter 3bio (FIG. 5) serves this purpose.

In another aspect of the invention, a method of making a solid substrate-bound transposase complex is provided. The method comprises forming a transposase complex comprising at least one transposase and at least one adapter oligonucleotide, wherein the adapter comprises a member of a specific binding pair, and combining the complex with a solid substrate to which is bound the other member of the specific binding pair under conditions where the specific binding pair members bind, to form a solid substrate-bound transposase complex. In embodiments where the complex comprises two or more adapters, it can be preferable that only one of the adapters comprises the specific binding pair member. Overall, it is important that if for example the complex is a dimer, adapters with a specific binding pair member would constitute about 50% of the adapters pool, regardless of whether or not all of the binding pair member is provided on one type of an adapter, or if half of the molecules of each type of adapter have a specific binding pair member. The number of specific binding pair members in each complex can be regulated based on the ratio between binding pair-tagged (e.g., biotinylated) and untagged adapters. For optimizing the ratios, different ratios should be used, e.g., 1:3, 1:2, 1:1, 3:1, 2:1, to achieve the desired DNA fragmentation. For instance, if a complex is predominantly a dimer, about 1:1 ratio could be expected to be optimal, but 1:3 ratio could be preferred where one molecule of tagged adapter is used in conjunction with three molecules of untagged adapter, as one molecule of the tagged adapter is sufficient to provide attachment of the complex to the solid support. Not necessarily, but contingent on the length and flexibility of the linkers, more than one point of attachment of the complex to solid support might restrict mobility of individual transposase subunits and their conformational changes that are believed to facilitate DNA fragmentation.

The method can be performed under any suitable conditions. Though it can be expected that the transposases and/or oligonucleotide adapters will be degraded during incubation with crude cell lysates, that complexes will be formed with genomic DNA present in the lysates, or that impurities, such as host cell genomic DNA, proteins, or other cellular matter, will inhibit the process of complex formation, surprisingly it has been found that transposase complexes according to the invention can be made in cell lysates without the need for prior purification of the transposase from the soluble cell materials. The method described herein allows for rapid production of complexes and capture of those complexes on a solid support without the need for laborious purification protocols.

In another aspect of the invention, a method of purifying transposase complexes is provided. In general, the method comprises forming a transposase complex comprising an adapter comprising a member of a specific binding pair, combining the complex with a solid substrate to which is bound the other member of the specific binding pair under conditions where the specific binding pair members bind, and separating the solid substrate-bound complex from at least some of the cellular material of the cell lysate. Removal can be by any suitable technique used in the art. For example, where the solid substrate is a bead, centrifugation can be used to separate solid substrate-bound complex from cellular material, or magnetic separation can be used with magnetic beads. Alternatively, where the solid substrate is a plastic surface, such as the well of a PCR plate, removal of unbound material from the well by aspiration can be used. As noted above, in embodiments where the complex comprises two or more transposases and two or more adapters, it is preferred that only one of the adapters per complex comprises the specific binding pair member. The number of specific binding pair members in each complex can be regulated based on the recognition sequence for each transposase.

Further purification beyond removal of at least some of the cellular material can be accomplished by washing the bound complexes using a suitable washing solution. For example, a suitable washing solution can include: 25 mM Bicine pH 7.93, 0.5 M KCl, 25% Glycerol, 5 mM EDTA, 4 mM Ditiothreitol, 0.4% Igepal CA-630. The washing solution may vary depending upon the transposase, but general guidelines are that, at the initial washes, using the same or similar solution as was used for the cell lysis is recommended in order to subject the complex to as little changes in pH, buffer, and salt concentration as possible. Further, the solution that is used in the last washing step should be similar to the solution used in the DNA fragmentation reaction in order to achieve better uniformity of samples.

The ability to obtain a solid substrate-bound transposase complex provides advantages not available to date. For example, as noted above, such bound complexes can be formed without an initial purification of the transposase complex. They thus can be formed in cell lysates or other complex mixtures. Binding of complexes without the need for a first purification step(s) allows for rapid purification of active transposases. The advantage of this feature is one way the present invention differentiates itself from other technologies. More specifically, because the transposases are bound to the appropriate DNA recognition sequences while in complex mixtures, such as cell lysates, they are expected to retain most of their activity during the purification process. Indeed, it has been seen that transposases retain a high level of activity through the purification process, as such complexes appear to be much more stable than transposase that is not bound with adapters. This feature allows for purification of wild-type transposases with wild-type or nearly wild-type activities, and is in direct contrast to prior work with Tn5 transposase, which is either purified as a wild-type enzyme with little or no activity, or which must be mutated to provide an active purified enzyme.

Purified solid substrate-bound transposase complexes are also immediately available for use, which is an advantage over prior technologies. Unlike prior technologies, the present invention provides solid substrate-bound transposase complexes that are loaded with adapters and are suitable for DNA fragmentation. Alternatively, in less preferred embodiments, the adapters, which function to stabilize the transposases during purification, can be removed from the solid substrate-bound transposase complexes, which not only releases the adapters from the transposases, but also releases the transposases from the solid substrate. As such, purified, soluble transposase can be achieved.

In exemplary embodiments, the solid substrate-bound transposase complexes are used for fragmentation of target DNA. In general, the method of fragmenting target DNA comprises contacting the target DNA with the solid substrate-bound transposase complexes under conditions where the transposases can cleave the target DNA, thus fragmenting the target DNA. Because the transposase complex is bound to the solid substrate via one of the adapters, during the process, the fragmented DNA replaces the transposase complex, thus yielding target DNA fragments that are bound to the solid substrate (see FIG. 1). The bound target DNA fragments can be used for any number of purposes, including, but not limited to amplification, sequencing, and detection of sequences of interest.

In one particularly preferred embodiment, the process of fragmenting target DNA can be linked to a method of amplifying the fragmented DNA (see FIG. 2). In these embodiments, solid substrate-bound transposase complexes are combined with target DNA under conditions that are suitable for DNA amplification, such as by PCR. The reaction mixture is incubated under conditions suitable for target DNA fragmentation (e.g., 5-30 minutes at 20° C.-55° C.) then, DNA fragmentation buffer is exchanged for PCR buffer and the fragments are subjected to conditions suitable for amplification, such as amplification by PCR.

Another aspect of the invention relates to kits. In general, kits according to the present invention comprise one or more components of at least one of the aspects of the invention described above that is useful in purifying transposases or transposase complexes, useful for fragmenting DNA, and/or useful for fragmenting and sequencing DNA. The components of the kits can be provided in, or bound to, one or more solid materials. For example, one or more components can be provided in a container, which can be fabricated from plastic materials and formed in the shape of microfuge tubes or sequencing plates (e.g., 84- or 96-wells per plate). Alternatively, one or more components can be provided as a substance bound to a solid support. For example, a transposase complex can be provided as a complex bound via a specific binding pair to a nylon strip or to the well walls of a plastic 84-well plate. Those of skill in the art are aware of numerous other equivalent containment materials and forms that can be used to contain the components of kits. As such, and exhaustive listing is not necessary herein.

In one embodiment, a kit according to the invention comprises one or more purified transposases of the invention. The transposase can be provided as a liquid solution (e.g., an aqueous or alcohol solution) in one or more containers. Alternatively, the transposase can be provided as a dried composition in one or more containers. In embodiments, two or more different purified transposases are provided in a single container or in two or more containers. Where two or more containers are provided, each container can comprise a single transposase, or one, some, or all of the containers can comprise a mixture of one, some, or all of the transposases.

In another embodiment of the kit of the invention, one or more oligonucleotide adapters are provided in one or more containers. The adapter can be provided as a liquid solution (e.g., an aqueous or alcohol solution) in one or more containers. Alternatively, the adapter can be provided as a dried composition in one or more containers. In embodiments, two or more different adapters are be provided in a single container or in two or more containers. Where two or more containers are provided, each container can comprise a single adapter, or one, some, or all of the containers can comprise a mixture of one, some, or all of the adapters.

In another embodiment of the kit of the invention, the kit comprises one or more purified transposases and one or more adapters. Preferably, at least one of the adapters comprises a recognition sequence for at least one of the transposases. More preferably, at least one adapter that has a recognition sequence for at least one transposase of the kit is provided. In this embodiment, it is to be noted that, because a particular transposase might recognize multiple related sequences, there does not need to be a one-to-one matching of transposases and adapters in the kit. As with other embodiments, in this embodiment of the kit, the transposases and adapters can be provided singly in different containers or any mixture of transposases and adapters can be provided in any number of containers.

In yet another embodiment of the kit of the invention, the kit comprises one or more transposase complexes. As with other embodiments, the complexes can be provided in a liquid composition or as a dried material. Furthermore, any number of different complexes can be provided in a kit. As above, the complexes can be provided singly in or on different containers or any mixture of complexes can be provided in or on any number of containers.

In an exemplary embodiment of the invention, the kit comprises one or more transposase complexes bound to a solid support such as beads or nanoparticles. In this embodiment, the solid support is considered to be a container for the complexes. The complexes are bound to the solid support by way of linkers, such as by a specific binding pair. In one exemplary embodiment, the complexes are provided bound to the surface of the wells of a PCR plate. In this embodiment, each well can comprise a single type of complex, or it can comprise two or more different complexes. In another exemplary embodiment of the kit, the complexes are provided bound to the surface of a nylon membrane, such as a nylon strip. In this embodiment, the complexes can be distributed about the membrane in any desired order and geometric shape and in any combination. For example, the membrane can have a single complex disposed on the membrane in a series of lines or dots. Alternatively, a series of lines or dots of different complexes can be provided (e.g., complex 1 is disposed on dot 1, complex 2 is disposed on dot 2, etc.). Yet again, mixtures of two or more complexes can be disposed on dots, lines, etc.

As noted above, in certain embodiments, it is preferable to provide two or more different transposase complexes having different recognition sequences in order to reduce GC vs. AT bias and thus to provide superior control of fragmentation of genomic DNA. In the context of kits comprising mixtures of transposase complexes, prior to creating the kit, one or more mixture can be optimized to minimize the bias for a particular target DNA by varying the ratios of complexes in the mixture. One skilled in the art can easily recognize how to create different mixtures of transposase-adapter complexes, how to immobilize them on solid supports, and how to apply them for target DNA fragmentation. The skilled artisan also knows how to amplify and sequence the fragments, analyze the sequencing data, select the mixture combination (ratio) with the least bias, and produce a kit based on that combination. It should be noted that different ratios can be recommended for different DNA targets and different kits can be manufactured for different types of targets. For instance, one skilled in the art can recognize that more transposase with AT bias should be used for AT-rich targets.

In certain embodiments of kits where two different transposases are present, the kits preferably comprise four different oligonucleotide adapters. Two of the adapters comprise a recognition sequence(s) for transposase "1", but only one of which comprises a specific binding pair member. The other two adapters comprise a recognition sequence(s) for transposase "2", but only one of which comprises a specific binding pair member. Through use of a combination of the adapters, transposase complexes can be formed and bound to a solid substrate via the specific binding pair members.

As mentioned above, the kits of the invention can comprise any number of substances that are useful for purification of transposases and complexes, or for practicing a method of the invention. Such substances include, but are not limited to: reagents (including buffers) for lysis of host cells, divalent cation chelating agents or other agents that inhibit nucleases, control DNA for use in ensuring that the transposase complexes and other components of reactions are functioning properly, DNA fragmenting reagents (including buffers), PCR reaction reagents (including buffers), and wash solutions.

The kits of the invention can be provided at any temperature. For example, for storage of kits containing transposases, adapters, or complexes in a liquid, it is preferred that they are provided and maintained below 0° C., preferably at or below −20° C., or otherwise in a frozen state.

As noted above, components of the kits are provided in containers or on solid substrates. The containers and solid substrates are provided in packaged combination in a suitable package, such as a box made of cardboard, plastic, metal, or a combination thereof. Suitable packaging materials for biotechnology reagents are known and widely used in the art, and thus need not be specified herein.

EXAMPLE

The invention will be further explained by the following Example, which is intended to be purely exemplary of the invention, and should not be considered as limiting the invention in any way. Furthermore, it is to be understood that not all of the process steps that are disclosed in this Example need be practiced to practice all aspects of the invention, and that some additional steps, as discussed above, can be practiced. For example, where the practitioner desires to obtain purified transposase complexes, the process steps discussed below relating to amplification of target DNA and sequencing of the amplified fragments need not be performed, but a step in which release of the complex from the solid support can be practiced instead. The skilled artisan will recognize where the process described below can be modified, based on the disclosure above and the knowledge held by that artisan, to arrive at different aspects of the present invention.

Sample Preparation for Sequencing Target DNA Using Transposases Attached to Solid Supports:

The following protocols and materials were used in the fragmentation of target DNA and the sequencing and analysis of the fragmented DNA. The skilled artisan will recognize that, while certain kits, products, and reagents of particular manufacturers are discussed, similar kits, products, and reagents can be substituted for those specifically discussed. Furthermore, other oligonucleotide adapters, having specificity for different transposases, amplification primers, sequencing primers, and/or tags can be substituted for those specifically discussed.

Dissolving Oligonucleotides and Preparing Adapters.

Dissolve all oligonucleotides represented in FIGS. 5 to 100 nm concentration in 10 mM Bicine-NH$_4$ pH 7.93, 20 mM KCl (add 10 ul of this buffer for each nM of oligonucleotide). In order to make partially double stranded adapters, mix equal volumes of oligonucleotide 3 bio with 3i0 to prepare adapter 3bio. Also mix equal volumes of oligonucleotides 8i1 and 8i0 in a separate vial to prepare adapter 8i0. Incubate both vials for 3 hours with a gradual decrease in temperature from 72° C. to 22° C.

Cultivation.

Seed 5 ml of LB medium supplemented with 100 ug/ml ampicillin with a fresh colony of recombinant E. coli that is expressing a transposase of interest, and incubate overnight on a shaker at 37° C. at 150 RPM. Dilute 5 ml of the overnight culture of E. coli expressing the transposase 1:10 with the same medium at room temperature. Incubate for 70 minutes at 37°, add 100 ul of 0.1M IPTG, and continue incubation for 5 hours at 32° C. If a transposase is predominantly soluble, e.g., Vibhar transposase, higher incubation temperature and shorter incubation time can be used, e.g., 3 hours at 37° C. If the transposase is only partially soluble and largely insoluble, longer incubation times and lower temperatures are recommended, e.g., overnight incubation at room temperature. Ampicillin is used in this example because the expression plasmids used for producing transposases also express beta-lactamase, which confers resistance to ampicillin. Other antibiotics can be used by those skilled in the art if the selection marker is different. Methods for constructing plasmids, recombinant E. coli strains, selection methods, methods for preparing the media and for growing E. coli cultures are known to those skilled in the art and described in detail in the literature, e.g., Sambrook et al., Molecular Cloning: A Laboratory Manual, Cold Spring Harbor Laboratory Press, incorporated herein by reference.

Harvesting Cells.

Harvest induced cell cultures after 5 hour post-induction by centrifugation at 4,500 RPM for 15 minutes in an Alegra X-15R centrifuge (Beckman Coulter, Brea, Calif.), wash each pellet with 50 ml 25 mM Bicine-100 mM NaCl, centrifuge again to collect the remainder of the washing buffer at the bottom of the tube, thoroughly remove the buffer and resuspend pellets from 50 ml cells in 450 ul of buffer Lx2 (50 mM Bicine-NH$_4$ pH 7.93, 0.5M KCl, 0.4% Igepal CA-630, 1 mM EDTA, 4 mM Dithiothreitol, 39% Glycerol). At this stage, resuspended cells can be frozen at −80° C. and stored for future use.

Obtaining Cell Lysates and Making Transposase-Adapter Complexes.

Disrupt cells by mild sonication on ice, e.g., sonicate twice at power 1.95, duty cycle 30, 40 pulses using Branson Sonifier model 250 (Branson Ultrasonics Corporation, Danbury, Conn.). Centrifuge in a microfuge at 4° C. for 40 minutes at 14,000 RPM. Collect supernatants (clarified lysates). Mix 400 ul of clarified lysate with 100 ul of glycerol, as about 50% concentration of glycerol is preferred for optimum loading of Vibhar and similar transposases with adapters. Dilute clarified lysates on ice 1:5 with cold buffer Lx1 (25 mM Bicine-NH$_4$ pH 7.93, 0.25M KCl, 0.2% Igepal CA-630, 0.5 mM EDTA, 2 mM Dithiothreitol, 50% Glycerol). Next, mix diluted lysates with adapters, e.g., mix 25 ul of adapter 3bio with 25 ul of adapter 8i1 and add 50 ul of the diluted lysate. Incubate at room temperature for 2 hours, add SAv beads and incubate at 4° C. overnight on a rotator. This results in attachment of transposase-adapter complexes to the beads.

Prior to adding, the beads are prepared as follows: magnetically precipitate 37.5 ul SAv beads (LoadStars 2.7 Streptavidin, Agilent Technologies) in 1.5 ml Eppendorf tubes and wash beads with 100 ul buffer Lx0.5 (buffer Lx1 diluted 1:1 with water). After the overnight incubation with the lysate, wash beads with attached transposase-adapter complexes three times with 1.5 ml of ice cold 25 mM Bicine-NH$_4$ pH 7.3, 0.1% Igepal CA-630, 20% Glycerol, 125 mM KCl, 2 mM DTT. Resuspend beads in 50 ul of the same buffer.

Fragmentation of Target DNA Using Transposase-Adapter Complexes Immobilized on Beads.

Combine 5 ul of target DNA (40 ug/ml in water), 5 ul of 5× Transposase buffer (125 mM Bicine-NH$_4$ pH 7.55, 100 mM MnCl$_2$, 125 mM Potassium Glutamate), 2 ul of water and 3 ul of the streptavidin beads with the transposase complex attached. Any target DNA can be used, for instance human, animal, plant, bacterial, or viral DNA at about the same concentrations. In this example, E. coli DNA (ATCC Cat#8739D-5, Genbank CP000946) which was resuspended overnight on rotator at 4° C. to concentration 40 ug/ml in water, or phage lambda DNA (Promega Corporation, Madison, Wis.) was used. It is suggested to set up a negative control with water instead of DNA to eliminate a possibility of contamination with the host cell DNA from crude cell lysates. Transposase reactions are performed on a rotator in order to keep the beads in suspension and to ensure accessibility of the target DNA to the immobilized transposase complex on the beads. 1013 SHEL LAB Hybridization Oven (Sheldon manufacturing, Inc., Cornelius, Oreg.) or any other rotator that provides for the required temperature can be used for this purpose. Rotate the reaction mixture at 45° C. for 1.5 hours at 10 RPM. Next, remove the vials with reactions from the rotator and magnetically wash the beads 1 time with 40 ul 1× PFUULTRA buffer, which is prepared by diluting 10× PFUULTRA™ HF reaction buffer (Agilent Technologies, Santa Clara, Calif.) 1:10 with water. Completely remove the buffer and resuspend the beads in 40 ul of 1× PFUULTRA buffer. These beads contain target DNA fragments as shown on FIG. 1D, that are flanked by adapters as shown on FIG. 5.

PCR Amplification and Sequencing.

Figure 6:
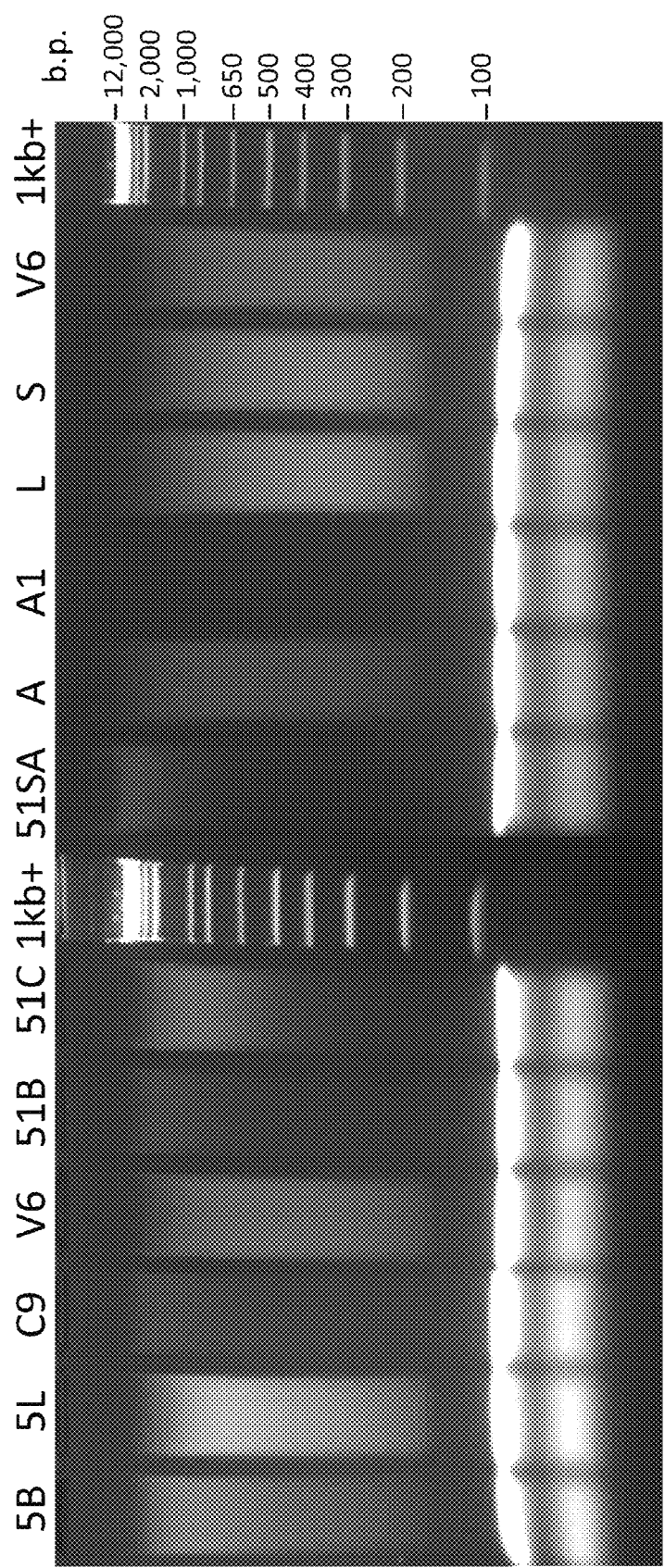
FIG. 6 depicts a picture of an agarose gel stained for DNA, showing that a variety of solid substrate-bound transposase complexes, including recombinant/chimeric transposase complexes, can be used to fragment target lambda DNA and amplify the fragmented DNA when bound to the solid substrate. For comparison, 1 kb+ DNA ladder (Life Technologies, Carlsbad, Calif.) was run on the gels alongside the fragments. Sample codes provided above the wells of the gel correspond to the codes provided in FIG. 4.
Figure 8:
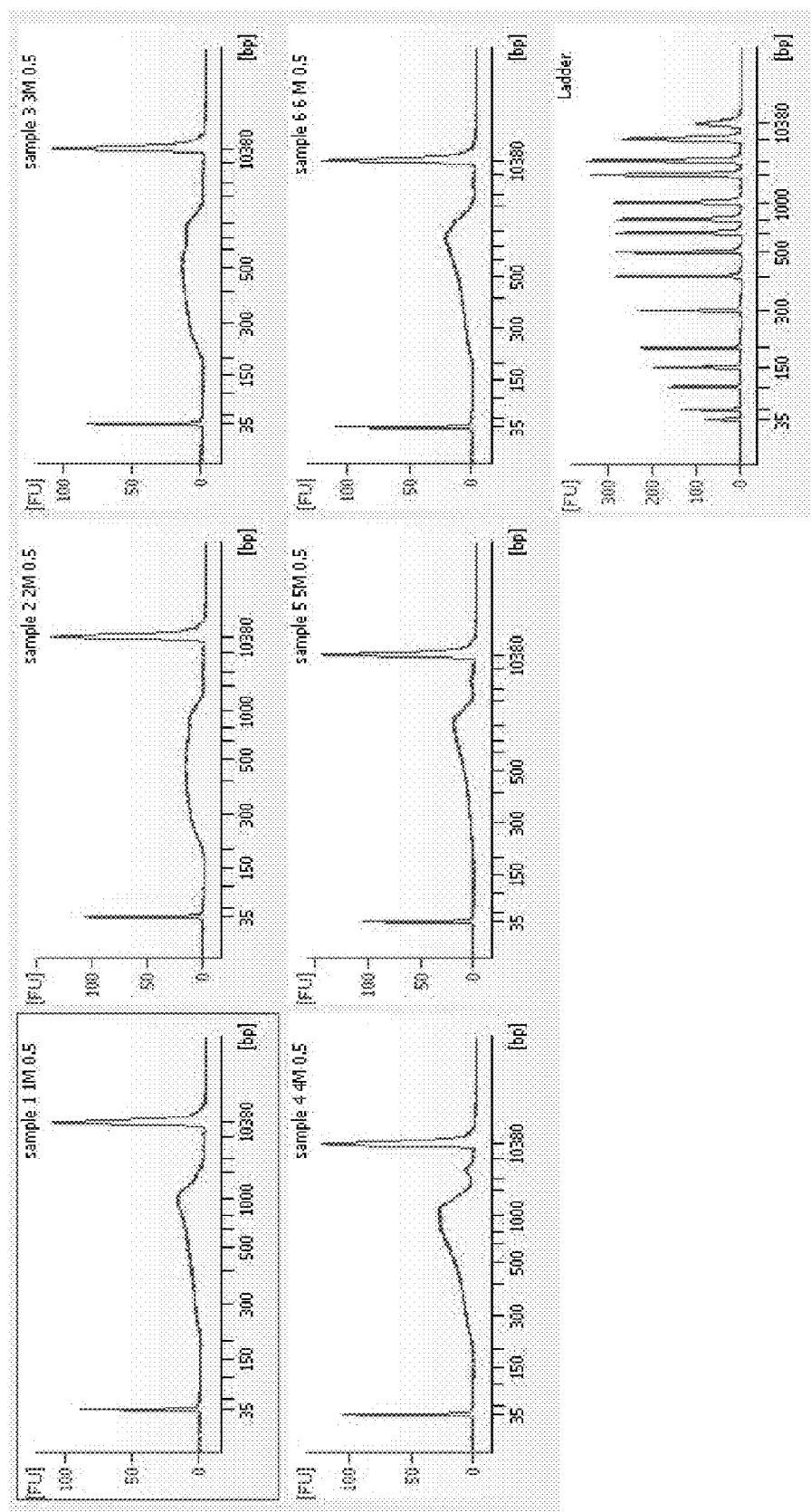
FIG. 8 shows Bioanalyzer Electropherograms of DNA fragments prior to submission for sequencing. Sample numbers correspond to the numbers provided in FIG. 4.
Figure 9:
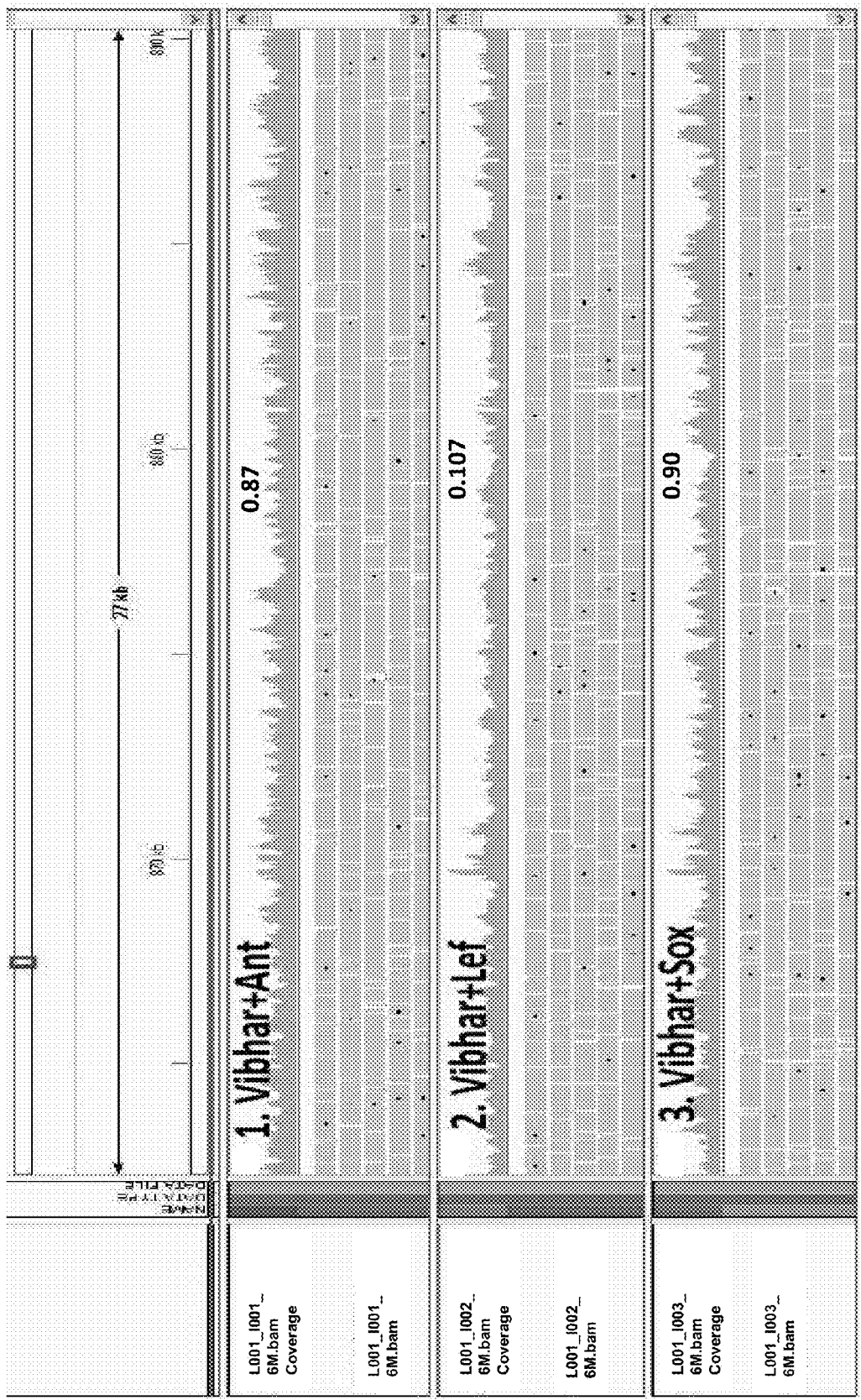
FIG. 9 shows sequenced DNA fragments of the *E. coli* genome (Genbank CP000946) obtained using different transposases, aligned onto the *E. coli* genome and presented via the Interactive Genomics Viewer program (Robinson et al., Nature Biotechnology 29, 24-26, 2011). Sample contents are indicated and correspond to the constructs provided in FIG. 4.
Figure 10:
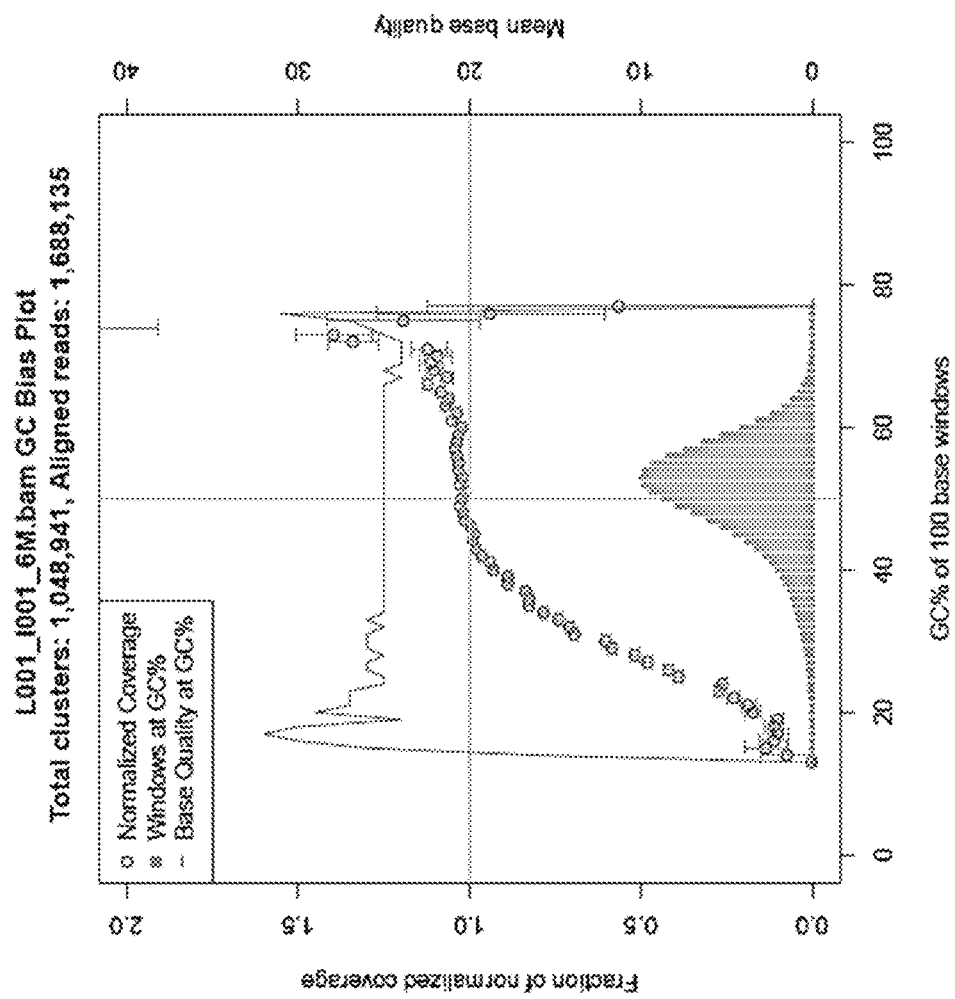
FIG. 10 shows GC bias plots of sequenced DNA fragments of the *E. coli* genome (Genbank CP000946) obtained using different transposases. Sample codes of the plots correspond to the codes provided in FIG. 4.

Prepare a PCR reaction mixture by combining 10 ul of the beads with attached target DNA fragments, 4 ul of 10× PFUULTRA™ HF reaction buffer, 5 ul of 10 mM dNTPs, 0.5 ul of 3iS primer, 0.5 ul of 8iS primer, 28.3 ul of water and 1.7 ul PFUULTRA (Agilent Technologies, Santa Clara, Calif.). Other thermostable DNA polymerases and their blends can be used also, e.g., PICOMAXX™ (Agilent Technologies, Santa Clara, Calif.). In this case 10× PICOMAXX™ buffer and PICOMAXX™ polymerase are used in the same amounts, but other components and PCR reaction conditions remain the same. Stir the mixture immediately before placing it into PCR amplifier to resuspend the beads, and amplify DNA fragments using the following program: hot start 45° C. for 2.5 minutes; hot start 95° C. for 3 minutes; followed by 9 cycles of denaturation at 93° C. for 40 seconds, annealing at 59° C. for 40 seconds, elongation at 72° C. for 3 minutes; end cycles, followed by a single elongation step at 72° C. for 10 minutes. The 8800 Thermal Cycler (Agilent Technologies, Santa Clara, Calif.) or any other instrument that provides for reaction parameters can be used for the amplification. Amplified DNA fragments are in solution, as shown on FIG. 2. Therefore the beads are discarded and the supernatant used for subsequent manipulations. At this point, the size range of the DNA fragments and their yield can be analyzed using Agarose gel electrophoresis (FIGS. 6 and 7) or using Bioanalyzer High Sensitivity DNA Chips (Agilent Technologies, Santa Clara, Calif.). Purify amplified fragments from primers and primer-dimers using AGENCOURT® AMPURE® XP magnetic beads (Beckman-Coulter, Brea, Calif.). To this end combine 50 ul PCR supernatant with 60 ul of beads suspension, mix by vortexing and incubate for 5 minutes at room temperature. Magnetically precipitate the beads and wash them twice on a magnetic rack (e.g. DYNAL® magnetic separation rack, Life Technologies, Carlsbad, Calif.) with 200 ul of 70% ethanol without disturbing the pellet. Air dry at room temperature for 15 minutes, elute DNA fragments by resuspending the beads in 50 ul of water and incubating the suspension for 2 minutes at room temperature. Magnetically precipitate the beads and harvest the supernatant. There are many suitable methods that are known to one skilled in the art for DNA fragment purification, for example gel purification, STRATAPREP® PCR purification kit (Agilent Technologies, Santa Clara, Calif.), QIAquick PCR purification kit (Qiagen, Valencia, Calif.). Perform a second round of PCR amplification as described above, but using a different pair of primers, i.e., AgP1 primer combined with AgP2 primer or with any of the i1-i8 indexed primers (FIG. 5). Purify PCR fragments as described above on AGENCOURT® AMPURE® XP magnetic beads, analyze the size range of the DNA fragments and their concentration and ensure that DNA fragments are purified from unused primers, e.g., using Bioanalyzer (FIG. 8) and sequence on any Illumina platform instrument (Illumina, San Diego, Calif.) using Rp1 and Rp2 primers and, in case the in indexed primers are used, also index read (InP) primer (FIG. 5). As shown in FIG. 9, the target genome is sequenced using this method of sample preparation for NGS. The method is also useful for selecting different transposases in respect of their different properties and suitability for the sample preparation. For example, as shown in FIG. 10, native *Photobacterium profundum* transposase (sample 4) and Vibhar/*Photobacterium profundum* hybrid transposase (sample 5) show less GC bias than other tested transposases and are more suitable for sample preparation with AT-rich target genomes.

As can be seen in FIG. 3, the solid substrate-bound Vibhar enzyme showed excellent activity on an external lambda DNA target. Importantly, no PCR fragments were obtained if external DNA target (phage lambda DNA) was not added, even if transposase was present in the cell lysates (lane 2). This demonstrates that PCR fragments were derived from lambda DNA that was added to the purified transposase/adapter complexes attached to SAv beads, rather than from *E. coli* DNA that was present in the lysates, but was removed in the process of purification of the transposase complex on the solid support. Fragment sizes were substantially between 100 bp and 1000 bp. The data also show that solid substrate-bound Vibhar, not some other enzyme, is responsible for the DNA fragmentation because no PCR fragments were generated in *E. coli* cell lysates that did not contain Vibhar transposase, with (lane 5) or without (lane 4) lambda DNA. FIG. 3 thus provides data showing that the process for purifying transposase complexes according to the invention not only provides purified solid substrate-bound complexes, but that these complexes are well suited for fragmentation of target DNA and PCR amplification. The complexes are thus active and are able to be purified in a relatively short process.

FIG. 3 indicates various advantages that the present invention provides over currently available technologies. Among the advantages are:

1) There appears to be a reduced or eliminated loss of transposase activity during purification, as compared to techniques known in the art at this time. Forming a transposase/adapter complex as a first step after lysis of cells appears to reduce or minimize losses of the enzyme activity during purification, and to produce a largely active preparation, rather than about 90% inactive, as obtained using traditional methods.

2) There is no need to provide the transposase with affinity tags, which might affect transposase folding, stability, and activity. There is also no need to use chromatography steps that require non-native conditions. In the present invention, the affinity tag (i.e., specific binding pair member; e.g., biotin) is attached to the oligonucleotide adapter rather than the transposase, and purification of the oligonucleotide-transposase complex is achieved under native conditions (i.e., cell environment) via specific binding pair member interactions (e.g., biotin-streptavidin). It is to be noted that an advantage of the biotin-streptavidin pair is that the interaction is very strong and reliable binding to solid support is easily achieved. However, for the same reason a biotin-streptavidin pair is often problematic in affinity purification of proteins, as proteins are difficult to elute from the support. This problem is elegantly resolved here, as the template attached to the solid support does not need to be eluted because it allows PCR amplification, and the PCR reaction products, not the bound template, are released into solution.

3) There is a drastic simplification of the DNA sample preparation for subsequent analysis, such as sequencing. Other methods require a multi-step process (up to 22 steps) to prepare fragmented DNA for sequencing. In contrast, the present invention provides a rapid and simple method to generate solid substrate-bound DNA fragments that are ready for amplification. In other words, fragmentation and amplification can be linked in a single reaction vessel and a single set of reagents. For example, PCR plates containing transposase-adapter complexes are filled with a master mix comprising PCR primers specific to the attached oligonucleotide adapters, a thermostable DNA polymerase, and buffer with approximately neutral pH. Magnesium or manganese ions are also included to initiate the DNA fragmentation reaction. After fragmentation, which is typically performed at about 20° C.-60° C., such as from 37° C. to 55° C., the reaction mix can simply be subjected to a PCR amplification run. In such a way, both reactions can be performed in the same container and in the presence of the same reagents. Indeed, if performed in a PCR machine, it is simply a matter of programming an initial incubation step prior to amplification.

4) Tagging of DNA fragments with specific DNA sequences to allow their amplification, attachment to sequencing chips, and with an optional bar code to track the origin of the sample can also be achieved at the first step. This contrasts with currently available methods, which require tagging after production of the DNA fragments, thus requiring yet an additional step.

Having shown that the Vibhar transposase can be produced and used to fragment DNA while bound to a solid substrate, additional transposases were obtained or created and tested to confirm the robustness of the present invention. To this end, GenBank was searched to identify sequences having amino acid identity to Tn5 and Vibhar, particularly in regions known to be involved in the structure and/or function of these two transposases. Several transposases were identified, including those described with reference to FIG. 4. The recognition sequences for each transposase were determined and are provided as SEQ ID NOs:25-34.

The wild-type sequences encoding these transposases were expressed recombinantly in *E. coli*, transposase-adapter complexes formed in cell lysates, complexes bound to a solid substrate, and bound complexes purified from cellular materials according to the protocol described above. Alternatively, chimeric transposases were created using sequences from two or more transposases. The chimeric transposases were then processed in the same manner as the recombinantly-produced wild-type sequences. The tested transposases are depicted graphically in FIG. 4. The amino acid sequences of each are provided in the legend of FIG. 4.

The substrate bound transposase complexes were then tested for their ability to fragment target DNA. Specifically, as can be seen from FIG. 6, numerous transposase complexes, including chimeric constructs, were produced and purified in an active form. This Figure indicates the breadth and robust nature of the present invention, and the wide applicability to many different transposases.

The Example provided above shows that the invention can be used to create DNA fragments suitable for DNA amplification using any number of transposases. To ensure that the quality of the DNA fragments is sufficiently high that the type of polymerase used to amplify the fragments is not important, the transposases depicted in FIG. 4 were expressed and purified in a solid substrate-bound form. Target DNA was fragmented using the solid substrate-bound enzymes, and the fragmented DNA amplified using two different DNA polymerases, and the amplification products subjected to agarose gel electrophoresis.

Figure 7:
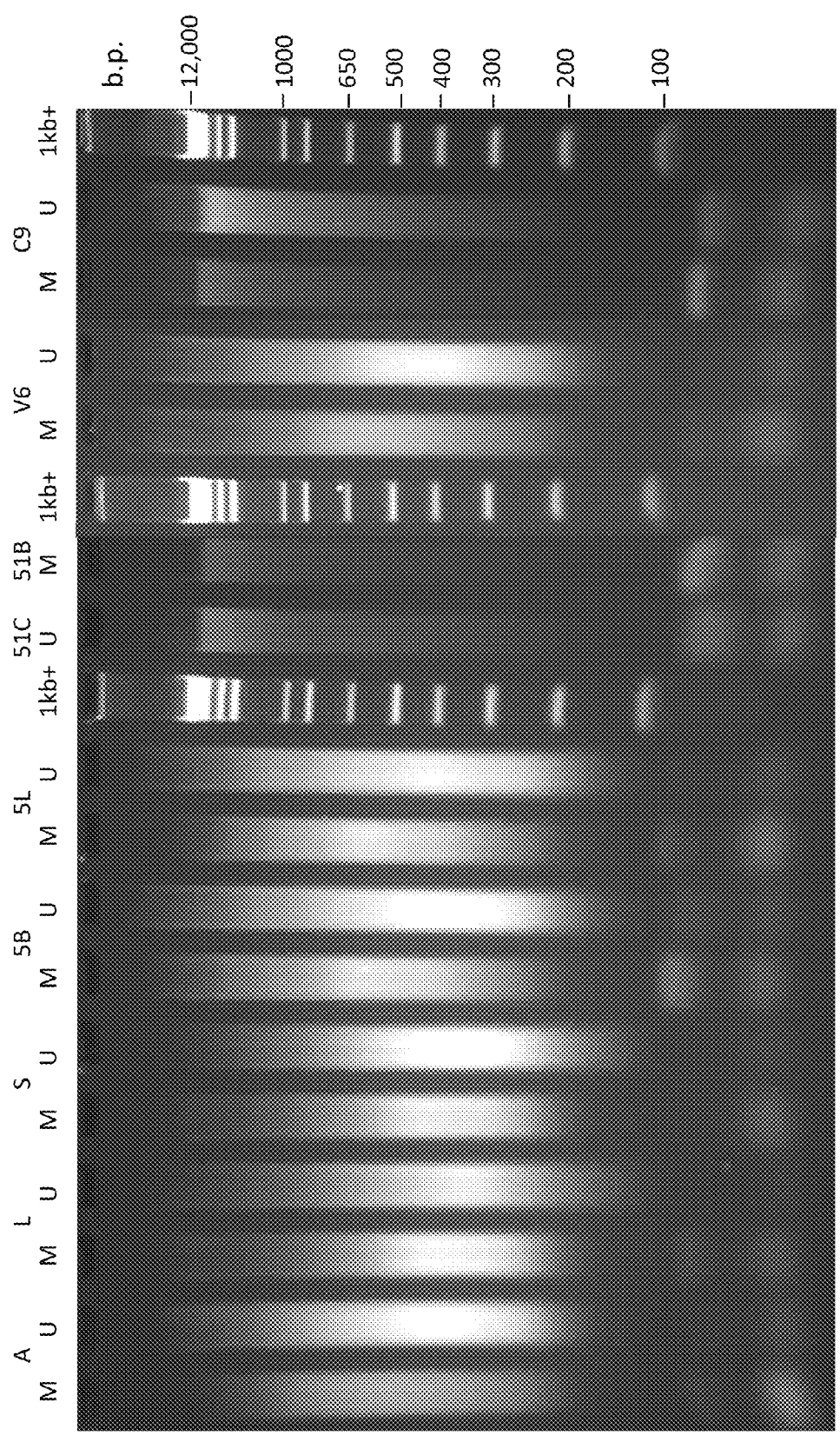
FIG. 7 depicts a picture of an agarose gel stained for DNA, showing that a variety of solid substrate-bound transposase complexes, including recombinant/chimeric transposase complexes, can be used to fragment target *E. coli* DNA and amplify the fragmented DNA when bound to the solid substrate, and that the amplification is not dependent on any particular polymerase or polymerase mix. Sample codes provided above the wells of the gel correspond to the codes provided in FIG. 4. Molecular weights are indicated on the right of the gel. M=amplified using PICOMAXX™ (Agilent Technologies, Inc.); U=amplified using PFUULTRA™ HF (Agilent Technologies, Inc.).

As can be seen from FIG. 7, the DNA fragments produced by all of the transposases tested was of high enough quality that both the PICOMAXX™ polymerase and the Pfu-Ultra polymerase could amplify the fragments. While there might be slight variations in the amounts of amplification products among the transposases and polymerases used, the data support a broad applicability of the invention for preparation of DNA fragments.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention.

The invention claimed is:

1. A solid substrate-bound transposase complex, wherein the complex comprises:
- a transposase component comprising a first transposase and a second transposase;
- an oligonucleotide adapter component comprising a first-oligonucleotide adapter and a second oligonucleotide adapter,
  - wherein each oligonucleotide adapter comprises at least one double stranded portion that contains a recognition sequence for a transposase of the complex, and
  - wherein the first oligonucleotide adapter is bound to the first transposase and the second oligonucleotide adapter is bound to the second transposase;
- a linker component comprising a specific binding pair, one of the members of the specific binding pair being bound to the first oligonucleotide adapter and the other member of the specific binding pair being bound to a solid substrate, wherein the second oligonucleotide adapter is not bound to a member of any specific binding pair; and
- a solid substrate.

2. The complex of claim 1, wherein the transposase component comprises two or more different transposases.

3. The complex of claim 1, wherein each adapter further comprises at least one single-stranded portion.

* * * * *

UNITED STATES PATENT AND TRADEMARK OFFICE
CERTIFICATE OF CORRECTION

PATENT NO. : 9,644,199 B2
APPLICATION NO. : 13/960837
DATED : May 9, 2017
INVENTOR(S) : Alexander S Belyaev It is certified that error appears in the above-identified patent and that said Letters Patent is hereby corrected as shown below:

On the Title Page

Item (56), in Column 2, under "Other Publications", Line 4, delete "Generatio" and insert -- Generation --, therefor.
Item (56), in Column 2, under "Other Publications", Line 18, delete "Nucleiod" and insert -- Nucleoid --, therefor.

In the Specification

In Column 5, Lines 58-59, delete "alfatoxin" and insert -- aflatoxin --, therefor.
In Column 10, Line 47, delete "8215," and insert -- R215, --, therefor.
In Column 10, Line 47, delete "8255," and insert -- R255, --, therefor.
In Column 17, Line 32, delete "Ditiothreitol," and insert -- Dithiothreitol, --, therefor.

In the Claims

In Column 63, Lines 24-25, in Claim 1, delete "first-oligonucleotide" and insert -- first oligonucleotide --, therefor.

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*